United States Patent
O'Farrell et al.

(10) Patent No.: US 11,459,601 B2
(45) Date of Patent: Oct. 4, 2022

(54) DIAGNOSTIC DEVICE AND SYSTEM

(71) Applicant: ALTRATECH LIMITED, Limerick (IE)

(72) Inventors: Brian O'Farrell, Watergrasshill (IE); Cian Desmond O'Sullivan, Limerick (IE); John O'Driscoll, Fountainstown (IE); Timothy Cummins, Cratloe (IE); Paul Free, Suffolk (GB); Moira Mccarthy, Kilbrittain (IE); John Walshe, Coachford (IE)

(73) Assignee: Altratech Limited, Limerick (IE)

( * ) Notice: Subject to any disclaimer, the term of this patent is extended or adjusted under 35 U.S.C. 154(b) by 445 days.

(21) Appl. No.: 16/647,795

(22) PCT Filed: Sep. 6, 2018

(86) PCT No.: PCT/EP2018/074058
§ 371 (c)(1),
(2) Date: Mar. 16, 2020

(87) PCT Pub. No.: WO2019/057515
PCT Pub. Date: Mar. 28, 2019

(65) Prior Publication Data
US 2020/0216884 A1    Jul. 9, 2020

(30) Foreign Application Priority Data

Sep. 20, 2017 (EP) .................................. 17192153
Sep. 20, 2017 (EP) .................................. 17192156
Nov. 21, 2017 (EP) .................................. 17202859

(51) Int. Cl.
*C12Q 1/6825* (2018.01)
*B01L 3/00* (2006.01)

(52) U.S. Cl.
CPC ...... *C12Q 1/6825* (2013.01); *B01L 3/502761* (2013.01); *B01L 3/502784* (2013.01);
(Continued)

(58) Field of Classification Search
CPC ......... B01L 2300/042; B01L 2300/047; B01L 3/502761; B01L 3/502784; C12Q 1/6816;
(Continued)

(56) References Cited

U.S. PATENT DOCUMENTS

| 4,822,566 A | 4/1989 | Newman |
| 5,164,319 A | 11/1992 | Hafeman et al. |

(Continued)

FOREIGN PATENT DOCUMENTS

| CN | 101724695 A | 6/2010 |
| CN | 102471051 A | 5/2012 |

(Continued)

OTHER PUBLICATIONS

Chang, 2013, A CMOS magnetic microbeaad-based capacitive biosensor array with on-chip electromagneitc manipulation, Biosnsors and Bioelectronics, 45:6-12.
(Continued)

*Primary Examiner* — Jennifer Wecker
*Assistant Examiner* — Kathryn Elizabeth Limbaugh
(74) *Attorney, Agent, or Firm* — Brown Rudnick LLP; Thomas C. Meyers

(57) ABSTRACT

A portable diagnostic device has a lysate stage with a port for receiving a sample and containing magnetic beads with a probe, and an outlet port. A series of assay stages are linked with the lysate vessel, each with a reservoir linked by channels. The final stage has a sensor for detecting beads attached to analyte molecules which have been conveyed according to attachment to probes on beads. Larger transport beads cause reporter beads which are tethered by target NA (Continued)

and probes to be transported to the final sensor stage, where they are released and detected when the transport beads have been removed.

25 Claims, 16 Drawing Sheets

(52) U.S. Cl.
CPC ...... *B01L 2300/042* (2013.01); *B01L 2300/047* (2013.01); *C12Q 2547/107* (2013.01); *C12Q 2563/143* (2013.01); *C12Q 2563/149* (2013.01)

(58) Field of Classification Search
CPC ............ C12Q 1/6825; C12Q 2547/107; C12Q 2563/143; C12Q 2563/149
See application file for complete search history.

(56) References Cited

U.S. PATENT DOCUMENTS

| | | | |
|---|---|---|---|
| 5,413,924 | A | 5/1995 | Kosak et al. |
| 5,679,519 | A | 10/1997 | Oprandy |
| 6,315,737 | B1 | 11/2001 | Skinner |
| 6,428,962 | B1 | 8/2002 | Naegele |
| 6,548,311 | B1 | 4/2003 | Knoll |
| 8,623,636 | B2 | 1/2014 | Fernandez Lopez et al. |
| 10,160,966 | B2 | 12/2018 | O'Farrell et al. |
| 10,738,348 | B2 | 8/2020 | O'Farrell et al. |
| 10,746,683 | B2 | 8/2020 | Cummins et al. |
| 2001/0055763 | A1 | 12/2001 | Singh |
| 2002/0168663 | A1 | 11/2002 | Phan et al. |
| 2003/0013185 | A1 | 1/2003 | Saraf |
| 2003/0059789 | A1 | 3/2003 | Efimov et al. |
| 2003/0129738 | A1 | 7/2003 | Sorenson et al. |
| 2004/0005582 | A1 | 1/2004 | Shipwash |
| 2004/0023253 | A1 | 2/2004 | Kunwar et al. |
| 2004/0058389 | A1 | 3/2004 | Wang et al. |
| 2004/0078219 | A1 | 4/2004 | Kaylor et al. |
| 2004/0086944 | A1 | 5/2004 | Grigg et al. |
| 2004/0161788 | A1 | 8/2004 | Chen et al. |
| 2004/0234970 | A1 | 11/2004 | Yoo |
| 2004/0235028 | A1 | 11/2004 | Franzen et al. |
| 2005/0069905 | A1 | 3/2005 | Myerholtz et al. |
| 2005/0218465 | A1 | 10/2005 | Cummins |
| 2006/0040286 | A1 | 2/2006 | Mirkin et al. |
| 2006/0105373 | A1 | 5/2006 | Pourmand et al. |
| 2006/0118494 | A1 | 6/2006 | Rundt et al. |
| 2006/0205061 | A1 | 9/2006 | Roukes |
| 2006/0205093 | A1 | 9/2006 | Prins |
| 2006/0281094 | A1 | 12/2006 | Squirrell et al. |
| 2007/0132043 | A1 | 6/2007 | Bradley et al. |
| 2008/0160622 | A1 | 7/2008 | Su et al. |
| 2009/0008248 | A1 | 1/2009 | Shimomura et al. |
| 2009/0035746 | A1 | 2/2009 | Ehben et al. |
| 2009/0127589 | A1 | 5/2009 | Rothberg et al. |
| 2009/0253120 | A1 | 10/2009 | Chae et al. |
| 2010/0019784 | A1 | 1/2010 | Wang et al. |
| 2010/0089769 | A1 | 4/2010 | Ulmer et al. |
| 2010/0227416 | A1 | 9/2010 | Koh et al. |
| 2010/0267162 | A1 | 10/2010 | Kartalov et al. |
| 2010/0291536 | A1 | 11/2010 | Viljoen et al. |
| 2011/0053788 | A1 | 3/2011 | Bamdad et al. |
| 2011/0124851 | A1 | 5/2011 | Guo |
| 2012/0073986 | A1 | 3/2012 | Jackson et al. |
| 2012/0197157 | A1 | 8/2012 | Ryan et al. |
| 2013/0046257 | A1 | 2/2013 | Beck et al. |
| 2013/0189687 | A1 | 7/2013 | Tanaka |
| 2015/0118743 | A1 | 4/2015 | Hanamura et al. |
| 2016/0095541 | A1 | 4/2016 | Wang et al. |
| 2016/0304941 | A1 | 10/2016 | O'Farrell et al. |
| 2017/0023512 | A1 | 1/2017 | Cummins et al. |
| 2019/0085319 | A1 | 3/2019 | O'Farrell et al. |
| 2019/0085320 | A1 | 3/2019 | O'Farrell et al. |
| 2020/0216884 | A1 | 7/2020 | O'Farrell et al. |

FOREIGN PATENT DOCUMENTS

| | | |
|---|---|---|
| CN | 103261892 A | 8/2013 |
| EP | 1595503 A2 | 11/2005 |
| EP | 1944368 A1 | 7/2008 |
| EP | 2233920 A1 | 9/2010 |
| JP | 2004-061144 A | 2/2004 |
| WO | 88/10272 A1 | 12/1988 |
| WO | 99/14596 A1 | 3/1999 |
| WO | 01/09388 A1 | 2/2001 |
| WO | 2006/071770 A2 | 7/2006 |
| WO | 2007/106579 A2 | 9/2007 |
| WO | 2009/111316 A2 | 9/2009 |
| WO | 2011/017660 A2 | 2/2011 |
| WO | 2012/028719 A2 | 3/2012 |
| WO | 2015/086652 A1 | 6/2015 |
| WO | 2015/086654 A1 | 6/2015 |
| WO | 2015/091139 A2 | 6/2015 |
| WO | 2016/091868 A1 | 6/2016 |
| WO | 2017/114746 A1 | 7/2017 |
| WO | 2019/057513 A1 | 3/2019 |
| WO | 2019/057515 A1 | 3/2019 |

OTHER PUBLICATIONS

Dynal, 1998, Biomagnetic Techniques in Molecular Biology, Technical Handbook, 3rd Edition, 4 pages.
Guo, Uric Acid Monitoring with a smartphone as the electrochemical analyzer, Anal Chem, 88(24):11986-11989.
Maarti, 1992, Agents That Increase the Permeability of the Outer Membrane, Microbiological Reviews, vol. 56 (3): 395-411.
Moreno-Hagelsieb, 2004, Sensitive DNA electrical detection based on interdigitaled A1/A12O3 microeleclrodes, Sensors and Actuators B, 98:269-274.
Moschou, 2013, Integrated biochip for PCR-based DNA amplification and detection on capacitive biosensors, SPIE Microtechnologies, vol. 8765, 87650L-8, 10 pages.
Nishiguchi, 2002, DNA Isolation Procedures, Methods and Tools in Biosciences and Medicine, Techniques in molecular systematics and evolution, pp. 249-287.
Prasad, 2012, Formulation and Characterization of Sodium Alginate g-Hydroxy Ethylacrylate Bio-Degradable Polymeric Beads: In Vitro Release Studies, J Polym Environ, 20:344-352.
Stagni, 2006, CMOS DNA Sensor Array With Integrated AID Conversion Based on Label-Free Capacitance Measurement, IEEE Journal of Solid-State Circuits; vol. 41(12):2956-2964.
Stagni, 2006, Fully Electronic CMOS DNA Detection Array Based on Capacitance Measurement with On-Chip Analog-to-Digital Conversion, Digest of Technical Papers, IEEE International Solid-Slate Circuits Conference, 10 pages.
Stagni, 2007, A Fully Electronic Label-Free DNA Sensor Chip, IEEE Sensors Journal, vol. 7(4): 577-585.
Stoner, Adsorption of Blood Proteins on Metals Using Capacitance Techniques, The Journal of Physical Chemistry; p. 1088.
Walsh, 1991, Chelex 100 as a Medium for Simple Extraction of DNA for PCR-Based Typing from Forensic Material, BioTechniques, 10:506-513.
International Search Report issued in PCT/EP2018/074058; dated Sep. 28, 2018.

DIAGNOSTIC DEVICE AND SYSTEM

FIELD OF THE INVENTION

The invention relates to human or animal medical diagnostics or health-status monitoring.

PRIOR ART DISCUSSION

WO2015086652 (Altratech Ltd) describes preparing a nucleic acid sample involving lysing cells and using PNA probes to capture RNA in the cells.

WO2015091139 (Altratech Ltd) describes preparing a nucleic acid sample involving the step of tethering PNA-coated beads.

WO2015086654 (Altratech Ltd) describes capacitive sensors arranged to detect and quantify an analyte in a liquid sample over a sensor surface.

The entire contents of these documents are incorporated herein by reference.

US2015/0118743 (Seiko Epson) describes a nucleic acid extraction device with a tube having a wax or oil, a washing liquid, a wax, an eluate, and a wax or oil.

WO2009111316 (Northwestern University) describes barriers used in sample separation, purification, and modification.

The present invention is directed towards providing a device and system for testing a sample such as a blood sample and providing clear diagnostic data or health data, in which:

- the device is compact and portable, with few components; and/or has the ability to detect and quantify single or multiple target nucleic acids, such as RNA (Ribonucleic Acid), or other microbiological entities, e.g. viral RNA from five or more species with replication and suitable controls; and/or
- has the ability to assay multiple RNAs; and/or
- the major parts of the device are fully synthetic (e.g. no enzymatic reagents) to allow for reproducibility, stability and simple logistics; and/or
- is inexpensive enough to be disposable; and/or
- the device reader avoids need for a service engineer.

SUMMARY

We describe a portable diagnostic device as set out in claim 1 and its subsidiary claims. We also describe in claim 64 and its dependent claims a diagnostics system incorporating a device and a reader for the device, and in claim 75 and its dependent claims methods for their operation.

In various aspects, we describe a diagnostic or nucleic acid quantitation device which has stages linked by channels with cross-sectional areas preferably in the range of 0.02 mm$^2$ and 1.5 mm$^2$, and more preferably in the range of 0.05 mm$^2$ to 0.8 mm$^2$. The channel walls are preferably thin (such as less than 3 mm) to allow for good thermal conductivity and penetration of magnetic fields. The channels and stages may be formed by a length of tubing in which the stages are defined by liquid barriers, or the channels may be conduits linking physically discrete stages. Magnetic particles used for capturing and transporting the analyte (transport or "T-beads") may be initially contained in a wax and bead matrix plug 104 which is solid at ambient temperature. The analyte is captured on the T-bead by a probe (Probe1) that is either pre-attached to the T-bead (e.g. covalent attachment of Probe1 to T-bead surface) or is added to the sample before addition of T-beads (e.g. a nanoparticle with both probe1 and another ligand on its surface, the latter mediating attachment to the T-bead). Where channel segments form stages they are preferably terminated and bounded by oil or other barrier liquid or gel which allows passage of analyte to the next stage. Cohesive forces between the water molecules exclude oil molecules (e.g. silicone oil or cycloalkanes) creating an aqueous phase/oil phase interface and barrier to the transition of hydrophilic molecules and hydrophilic particles. Entropy determines that the surface areas of the interfaces are kept to a minimum.

The arrangement of the inlet provides for concentration and separation of the analyte from other material as it passes through a liquid barrier which may be formed when the wax or oil becomes molten. The aspect of the device being portable and having an inlet as described and assay stages including a sensor allows the device to be self-contained. It may receive any of a range of samples without pre-treatment, especially where the inlet is arranged to perform lysing.

Magnetic particles ("T-beads") suspended in the aqueous phase (i.e. they have a hydrophilic surface) experience a force when an external force is applied, e.g. by a permanent magnet. As the particles are concentrated and are moved towards the aqueous/oil interface, this force is now exerted on the interface. Frictional forces on the bolus are minimised by keeping the particles away from the microfluidic channel wall using magnets and by use of Teflon-coated microfluidics. An aqueous bolus forms around the magnetic particles as the magnetic force pulls them into the oil. Interfacial tension maintains the bolus of water (and any impurities therein) around the magnetic particles. Entropy determines that the surface area of this new aqueous/oil interface is kept to a minimum so this bolus is very small (100-500 nl). This minimises the volume of liquid and the amount of impurities carried with the magnetic particles whereas all captured analyte is maintained on the surface of the particles. The analyte captured on the magnetic particles is concentrated in this bolus. They are also concentrated relative to any impurities.

Probes and/or transport beads may be microencapsulated (e.g. ethyl cellulose, polyvinyl alcohol, gelatin, sodium alginate) prior to being incorporated in a wax. This may provide for better stability and controlled release of the particles during the assay.

The probe may also contain cell-penetrating peptides (e.g. trans-activating transcriptional activator TAT) to facilitate cellular uptake prior to lysis. This limits exposure of the NA target to nucleases prior to lysis. This would be particularly beneficial in the case of PNA probes wherein nucleases do not recognise the PNA-NA duplex. The probes could be bound to particles or biotinylated for capture by streptavidin-coated beads.

The device may be used by external application of heat either manually or in an automated manner in a reader, and likewise movement may be caused magnetically either manually or in an automated manner.

There may be a first wash stage in which transport beads, "T-beads", are actively mixed using external magnets to release any non-target biological material which may have been carried within the bolus through a wax barrier from a lysis stage.

There may be a reporter probe attachment stage for use after washing of the analyte has been completed. This may contain a PNA probe (Probe2) which is complementary to a different section of the target NA than the original Probe1. The reporter Probe2 may be covalently attached to a reporter, such as a bead ("R"-bead). These R-beads may be smaller in diameter and are less magnetically susceptible than the T-beads. T-beads may be mixed within this reservoir, and if any target NA is present on the T-beads they bind and become attached to PNA Probe2 on the R-beads. This binding of the two probes across the same NA results in the T-beads and R-beads being tethered together only if the NA target is present. The sandwich comprises: T-bead—Probe1—Target NA—Probe2—R-bead.

The T-beads may be once again magnetically aggregated and removed into a second wash stage at which they are once again mixed and separated into solution, this time to release any non-attached R-beads which may have been carried through from the previous capture phase. The T-beads may then be aggregated once again and pulled through the oil barrier 112 into a sensor. There is now a 1:1 ratio of R-beads to NA targets. This is because the R-beads can only get from one reservoir to another reservoir if tethered to the T-bead by the Probe1—target NA—Probe2 sandwich.

The T-beads may be agitated over the sensor, such as by being magnetically moved over the surface of the sensor. The R-beads are separated from the T-beads and NA. This may be accomplished by application of heat to melt the PNA-Probe2 links to the NA, or by chemically destroying the NA target, thus breaking the tether between the two beads. The magnetic T-beads can now be pulled away either in the same direction or alternatively back into the previous stage for a second time. This leaves the R-beads over the sensor surface.

The Probe2 heating temperature to separate the second probes is typically 60° C. to 85° C., but could be 40 to 99° C., depending on its exact sequence which affects hybridisation strength. Short probes may be used for Probe2 to make this heat separation step easier without losing specificity. This temperature may be achieved by placing the device substrate on a hot plate, by "on-chip" heating and/or or by using an induction coil, which enables magnetic induction heating of ferrite R-beads, in a manner such as described in U.S. Pat. No. 5,378,879.

The presence of the isolated R-beads on the sensor indicates the presence of target NA in the original sample. In some examples, multiple NA targets could be targeted in parallel using the above approach, e.g. for detecting two types of virus at the same time (HIV_T-bead—HIV_Probe1—HIV_Target NA—HIV_Probe2—HIV_R-bead; HCV_T-bead—HCV_Probe1—HCV_Target NA—HCV_Probe2—HCV_R-bead). This results in two types of R-beads arriving on the sensor. The sensor can determine the quantities of each type of R-bead. Alternatively, the T-bead could have both HIV_Probe1 and HCV_Probe1 but with separate HIV_R-bead and HCV_R-bead.

A control NA to allow accurate quantitation of the target NA(s) could include endogenous controls such as 18S ribosomal RNA or the expression levels of a housekeeping gene such as SOX21. Processing of the control NA would be as per the descriptions of target NAs herein. An artificial control such as an armored RNA HIV could be used as well or instead of the endogenous controls. SOX21 is a "housekeeping gene" which is highly conserved across eukaryotic species.

The sensor may have at least two sensor regions with PNA probes which are complementary to PNAs on the R-beads so that each type of R-bead becomes hybridised to the correct sensor. The PNA probes on the sensor may be complementary to the HIV_Probe2 and HCV_Probe2.

Alternatively, the PNA probes on the sensor may be complementary to a standard PNA probe on each type of R-bead. These R-beads would then be additionally functionalised with HIV_Probe2 and HCV_Probe2. As the sensors come manufactured with standard PNAs, this approach allows more rapid assay development.

The sensor may include a semiconductor capacitance sensor chip mounted in the encapsulated microfluidic structure having a high-resolution sigma-delta capacitance-to-digital converter, calibration memory, and digital processing circuitry, including I2C serial communication. Terminals may connect the chip to an external reader or computer. A first "wet-capacitance" reading is taken by the sensor chip, of the R-beads in liquid. This provides a baseline reference calibration capacitance. After the liquid evaporates, a second "dry capacitance" reading is taken of the R-bead capacitance. Due to their dielectric constant being higher than air, any R-beads on the sensor surface give a capacitive signal, e.g. 1 fF (delta capacitance versus dry air) for 200 beads, as shown in FIG. 19 of WO2015086654.

Sample treatment (e.g. a hot plate which can be adjusted to specific temperatures) may be performed so as to only cause lysis of certain types of cells or capsids in the sample. Such an adjust may in one example be applying a stress (in this case heat) to all cells within a blood sample wherein white blood cells (containing DNA) can respond to prevent lysis whereas other cells and, particularly, viral particles are lysed. This is advantageous where the white blood cells contain retroviral DNA which can confound an assay for retroviral RNA. This retroviral DNA will not be available within the lysate produced here.

A lysis buffer can be adjusted so as to only cause lysis in certain target cells or capsids in the sample. This adjustment may for example involve a drug designed to bind to a particular protein target on the viral surface which damages membrane integrity. Blood may pass through immunomagnetic beads suitable for removing certain fractions of the blood prior to application of the sample to the device (e.g. Whole Blood MicroBeads Miltenyi Biotec). The blood may pass through a bed of resinous beads which may be functionalised (e.g. Chelex) or coated in reagents to help prevent clotting (other chelating agents such as EDTA or citrate).

These beads could also be functionalised with ligands for selective capture of certain fractions of the blood after application of the sample to the device (following same principle of Whole Blood MicroBeads Miltenyi Biotec). The beads may be of a high density and gravity will hold these in situ, particularly where this section is vertical.

In one aspect, a portable diagnostic device comprises:
  a series of assay stages, each with a reservoir linked by channels; and
  at least one of the assay stages including a sensor or an interface to a sensor for detecting analyte which is optionally attached to beads.

The device may further comprise a lysate stage for receiving a sample and containing magnetic beads with a probe, and a lysate agent and an outlet to the assay stages. Preferably, the lysate stage comprises a liquid-liquid purification stage in an outlet port, the purification stage comprising a wax plug including embedded magnetic beads for attachment to target analyte, providing for concentration and separation of the analyte from other material as it passes through the liquid barrier. The lysate stage outlet port may be funnel-shaped and the wax plug is a friction fit within the lysis vessel at the outlet port.

The magnetic beads may be embedded in a wax plug comprising a composite of polystyrene and ferrite nanoparticles. Preferably, at least one assay stage is configured to carry out a wash. Preferably, said wash stage is arranged to provide interfacial tension and capillary forces between the water and oil/wax barriers, keeping the aqueous solution reservoirs isolated from each other.

Preferably, a single, cohesive oil and/or wax component is used as a barrier in non-sequential assay steps. Preferably, the wash stage comprises a reservoir with a buffer such as aqueous solution, the reservoir being arranged to allow mixing to facilitate beads to homogenise in the buffer.

Preferably, the wash assay stage is connected by a channel to a reporter bead (R-bead) assay stage. Preferably, the reporter bead assay stage contains magnetic reporter beads which have less magnetism than transport beads, and the reporter beads have attached a second PNA-probe ("Probe2") complementary to target nucleic acid of the analyte, such that if the target NA is present attached to a transport bead (T-bead), a T-bead-R-bead tethered sandwich is formed within the assay stage. Preferably, the reporter beads have a size in the range of 0.1 μm to 0.5 μm.

The reporter bead assay stage may be connected by a channel to a reporter bead wash stage, for removing any excess R-beads. Preferably, the reporter bead wash assay stage is connected by a channel to a next assay stage which comprises the sensor.

Preferably, the sensor comprises a capacitive sensor arranged to detect capacitance of contents of an associated reservoir. The sensor may be adapted to perform detection based on capacitance to detect the number of reporter beads on the sensor surface, in which the reporter beads represent quantity of analyte such as target NA. Preferably, the sensor is adapted to perform detection of a wet sample and/or to perform detection of a dry sample. Preferably, the device further comprises an agitator for agitation of analyte over the sensor. Preferably, the agitator comprises a piston for pushing and pulling analyte over the sensor, and such a piston may be driven by a screw mechanism, and the piston may be arranged to push a reference fluid over the sensor, and the sensor may be a capacitive sensor and the piston is configured to push a gas with a known dielectric constant over the sensor.

Preferably, the sensor comprises a processor configured to store instructions and data required for controlling a reader and conducting the assay, optionally including instructions for actuator movements and temperature cycles. Preferably, said processor is configured to drive the reader so that assays are conducted automatically on insertion of the device into the reader. The sensor may be arranged to read beads on its surface against a background of an organic liquid having a low dielectric constant.

Preferably, the sensor comprises PNA probes which are complementary to a standard PNA probe on each type of R-bead, and the R-beads are additionally functionalised with HIV_Probe2 and HCV_Probe2. The sensor may comprise electrodes arranged to act as a trap for beads such as reporter beads. Preferably, the trap comprises electrodes arranged perpendicular to a flow of beads and controlling the pitch of the electrodes so that only the small R-beads can fit between them.

Preferably, the device comprises a waste chamber with a vent region, into which displaced liquid such as molten wax; chip reservoir buffer; surfactant; and any gas, may be pushed. Preferably, the expansion chamber contains a volume of sterile gas which may be pushed in front of this liquid through a filtered vent to the environment.

The device may further comprise a heater for heating sample in the lysis stage and/or analyte in at least one assay stage. Preferably, the device channel comprises a heterogeneous thermally-conductive matrix, and optionally also includes a hydrophobic coating.

Preferably, the device is configured to fit into a reader to form a sensing system, and optionally the device includes a processor configured to communicate with the reader to provide assay instructions and data so that that an assay is controlled by the device. Preferably, at least some of the channel is exposed to allow magnetic movement of beads by a magnet, and optionally at least some of the channel is exposed to be heated by a heater, and preferably has a thin wall of less than 1 mm for ease of heat transfer. The device may include a processor configured to store and communicate a unique identifier for a sample, and optionally this identifier is correlated with a physical identifier printed on the device housing for reading by for example a 1D or 2D code reader.

The device may comprise an inlet stage comprising a filter in a chamber and a piston arranged to drive blood or other sample through the filter. Preferably, the filter is in a first chamber and the piston is in a second chamber having a volume communicating with a volume in the first chamber upstream of the filter.

Preferably, the second chamber is situated laterally of the first chamber. Preferably, the volumes of both the first and second chambers, both upstream and downstream of the filter, are under vacuum. The first chamber may include a membrane which can be pierced to take a sample. The first chamber may include a lysis agent. Preferably, the inlet stage includes a bubble entrapment chamber. Preferably, the bubble entrapment chamber is aligned on an axis with the membrane, and said axis is at an angle to an axis between the piston and the filter. Preferably, said angle is approximately 90°.

We also describe a portable diagnostic system comprising a device of any embodiment and a reader, the reader comprising:
  a support for receiving the device;
  magnets on a drive to convey beads through the assay stages of the device;
  a heat source;
  a means of connection with the sensor of the device, or a sensor for coupling with the sensor interface of the device, and
  a controller.

Preferably, the magnet drive comprises at least one arm arranged to move alongside the device. There may be at least two drive arms, arranged to move on opposed sides of the device. Preferably, the heat source is a thin foil heater and/or an overlay moulded to the device. Preferably, the magnets include a conical magnet wherein magnetic field lines are concentrated at an apex of the magnet. The magnets may be arranged to have a shape such as conical and/or orientation to provide a steep gradient in magnetic field for at least one assay stage.

The magnets may be mounted to be separated by a distance in the range of 5 mm to 20 mm from the device. The magnets may have a drive to vary separation of the magnets from the device, for analyte mixing. Preferably, the magnets have a drive for oscillating a magnet back and forth against another static magnet. Preferably, the magnets have a drive for rotating a magnet to create an oscillating magnetic field on one side of a channel. The magnets may have a drive with a static magnet on one side and an oscillating magnet on the opposed side of a channel. The heater may comprise a point heater on moveable arms. Preferably, the sensor is arranged to read beads on its surface against a background of an organic liquid such as ethanol.

We also describe a diagnostic method carried out by a system of any embodiment, the method comprising the steps of:

introducing a sample into the lysate stage and lysing the sample in the lysate stage to provide an analyte, or introducing a previously-lysed analyte into the device;

conveying the analyte through the assay stages within the device wherein movement and temperature of stages of the reader unit are controlled, and detecting analyte at the sensor.

Preferably, heat is applied to the lysate stage in order to melt a wax plug, resulting in an outlet port of the lysate stage becoming unblocked. Preferably, the beads are released from the wax plug, and enter the stage main body. Preferably, magnetic beads bind and capture target NA of the blood sample, in the lysate stage.

The lysate stage may contain transport magnetic beads (T-beads), PNA probes, and target nucleic acid. Preferably, the magnetic drive moves so as to magnetically move the beads from the lysate stage to a wash assay stage. Preferably, these transport beads travel out of the lysis stage and into a channel microfluidic containing molten wax in a contiguous column which has connection to aqueous reservoirs and the interfacial tension and capillary force keep assay stage reservoirs isolated from each other.

Preferably, neutral, non-functionalised magnetic beads are included which play no part in molecular binding, but provide for stabilisation to help the transport beads break the interfacial tension by their greater mass and responsiveness to the external magnetic field. Preferably, in the wash assay stage, any cellular debris or contaminants are removed from the sample.

Preferably, the magnetic drive moves so as to magnetically move the beads from the wash assay stage to a reporter bead assay stage. Preferably, the reporter bead assay stage contains smaller 'reporter' beads (e.g. 0.5 µm), which have attached a second PNA-probe ("Probe2") complementary to the target nucleic acid, and if the target NA is present, a T-bead R-bead tethered sandwich is formed within the reservoir.

Preferably, the magnetic drive moves so as to magnetically move the beads from the reporter bead assay stage to a reporter bead wash assay stage bringing with them any R-beads which have become tethered. Preferably, in the reporter bead wash assay stage, any excess R-beads are removed resulting in a 1:1 ratio of R-beads and NA targets being moved on from this point.

The sensor may comprise a capacitive sensor. Preferably, in the sensor assay stage, heat is applied to the reservoir to separate the T-beads. Preferably, T-beads are magnetically moved to a waste reservoir before sensing. Excess liquid may be evaporated and transported to a separate reservoir. The sensor may detect capacitance. Preferably, a capacitance reading corresponds to reporter beads on the sensor surface. The reading may for example indicate the presence of a viral infection. The sensor may be functionalized with for example PNA probes.

Preferably, PNA and transport beads are microencapsulated (e.g. ethyl cellulose, polyvinyl alcohol, gelatin, sodium alginate) prior to being incorporated in the wax of the lysis stage.

The lysis buffer may be adjusted so as to only cause lysis in certain target cells or capsids in the sample, and optionally this adjustment involves a drug to bind to a particular protein target on the viral surface which damages membrane integrity.

Preferably, the probe also contains cell-penetrating peptides (e.g. trans-activating transcriptional activator TAT) to facilitate cellular uptake prior to lysis, limiting exposure of the NA target to nucleases prior to lysis.

A heater may be adjusted to specific temperatures so as to only cause lysis of certain types of cells or capsids in the sample. Point heaters may be placed on movable arms, for more accurate heating control. Preferably, the adjustment includes applying a stress such as heat to all cells within a blood sample wherein white blood cells (containing DNA) can respond to prevent lysis whereas other cells and, particularly, viral particles are lysed.

Preferably, a blood sample passes through immunomagnetic beads suitable for removing certain fractions of the blood prior to application of the sample to the device (e.g. Whole Blood MicroBeads Miltenyi Biotec).

Preferably, blood passes through a bed of resinous beads which may be functionalised (e.g. Chelex) or coated in reagents to help prevent clotting (other chelating agents such as EDTA or citrate). Preferably, these beads are functionalised with ligands for selective capture of certain fractions of the blood after application of the sample to the device. Preferably, the beads have a density such that density and gravity will hold these in situ, particularly where this section is vertical.

Organic solvents may be used such that low density allows gravity to assist R-beads to drop across (vertical configuration) or down (horizontal configuration) on to the chip faster due to their lower buoyancy in the alcohol solution. This is desirable for some applications. Multiple targets may be targeted in parallel by providing a plurality of types of reporter beads in an assay stage so that a plurality of two types of reporter beads arriving on the sensor and the sensor determines the quantities of each type of reporter bead. Preferably, reporter beads are produced using a fluidic system to be doped with materials such as Titanium dioxide or Barium titanate to give a strong signal to a capacitance sensor.

PNA probes on the sensor may be complementary to a standard PNA probe on each type of R bead, and the R-beads are additionally functionalised with HIV_Probe2 and HCV_Probe2. As the sensors come manufactured with standard PNAs, this approach allows more rapid assay development. Preferably, transport beads which are magnetic and buoyant in water are manipulated using external magnetic fields within solutions less dense than water (e.g. 20% ethanol).

Preferably, the method includes multiplexing of analytes in the device. Preferably, the sensor comprises at least two sensor regions with PNA probes which are complementary to PNAs on the R-beads so that each type of R bead becomes hybridised to the correct sensor.

The sequence of steps for an assay may be driven by a processor of the device. Preferably, the device includes a stored and preferably encoded identifier for a sample which it has received and this is communicated either by physical terminals or wirelessly by the device to the reader. Preferably, the identifier is correlated with a device or sample identifier physically printed on the device housing, such as in a code such as a 1D code or a 2D code.

DETAILED DESCRIPTION OF THE INVENTION

The invention will be more clearly understood from the following description of some embodiments thereof, given by way of example only with reference to the accompanying drawings in which.

Figure 9B:
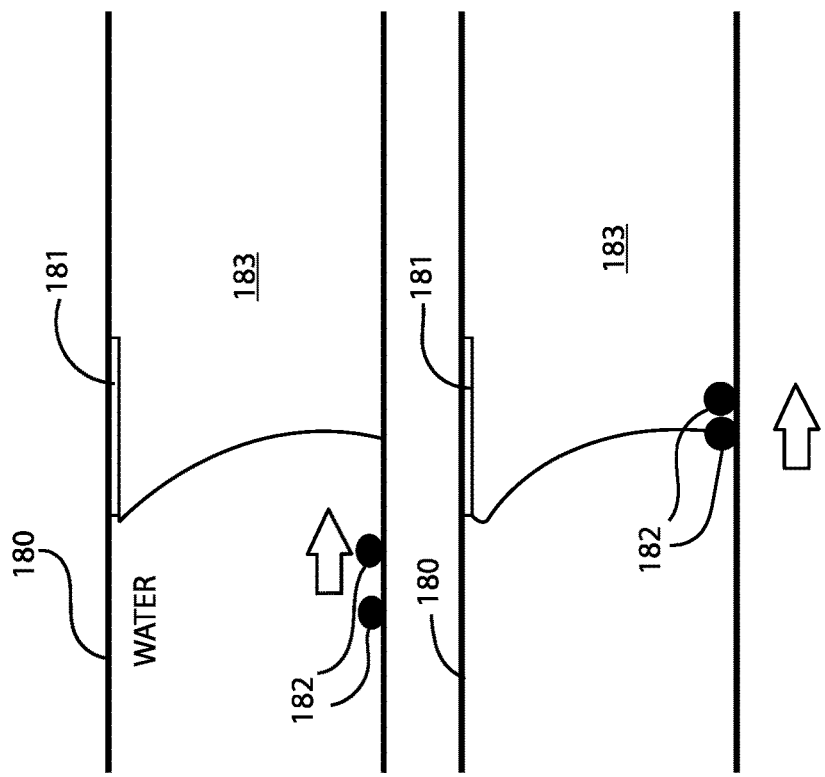
Figure 9A:
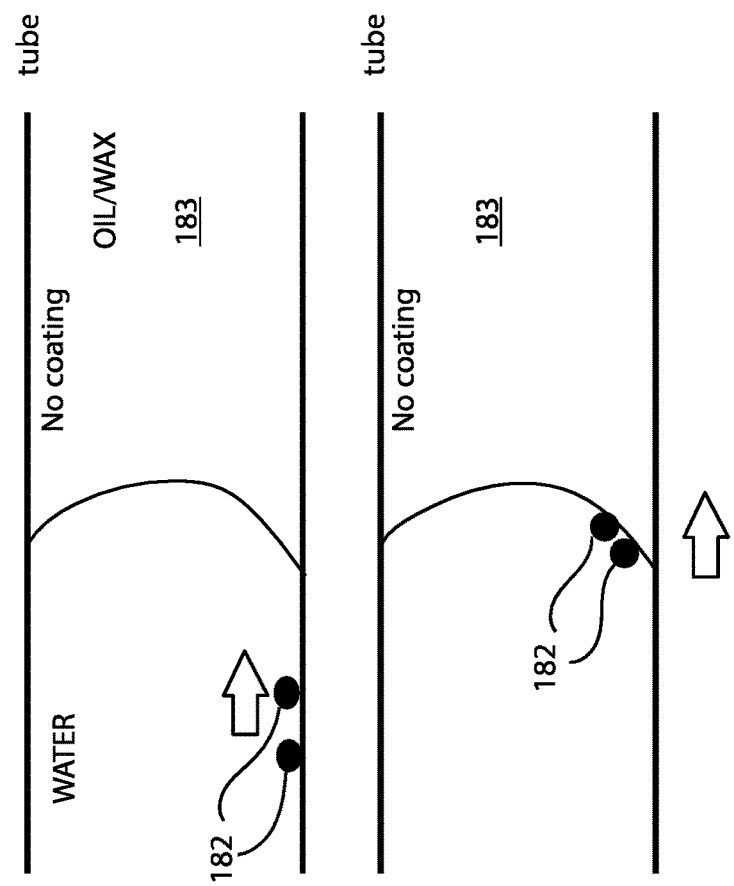
Figure 10:
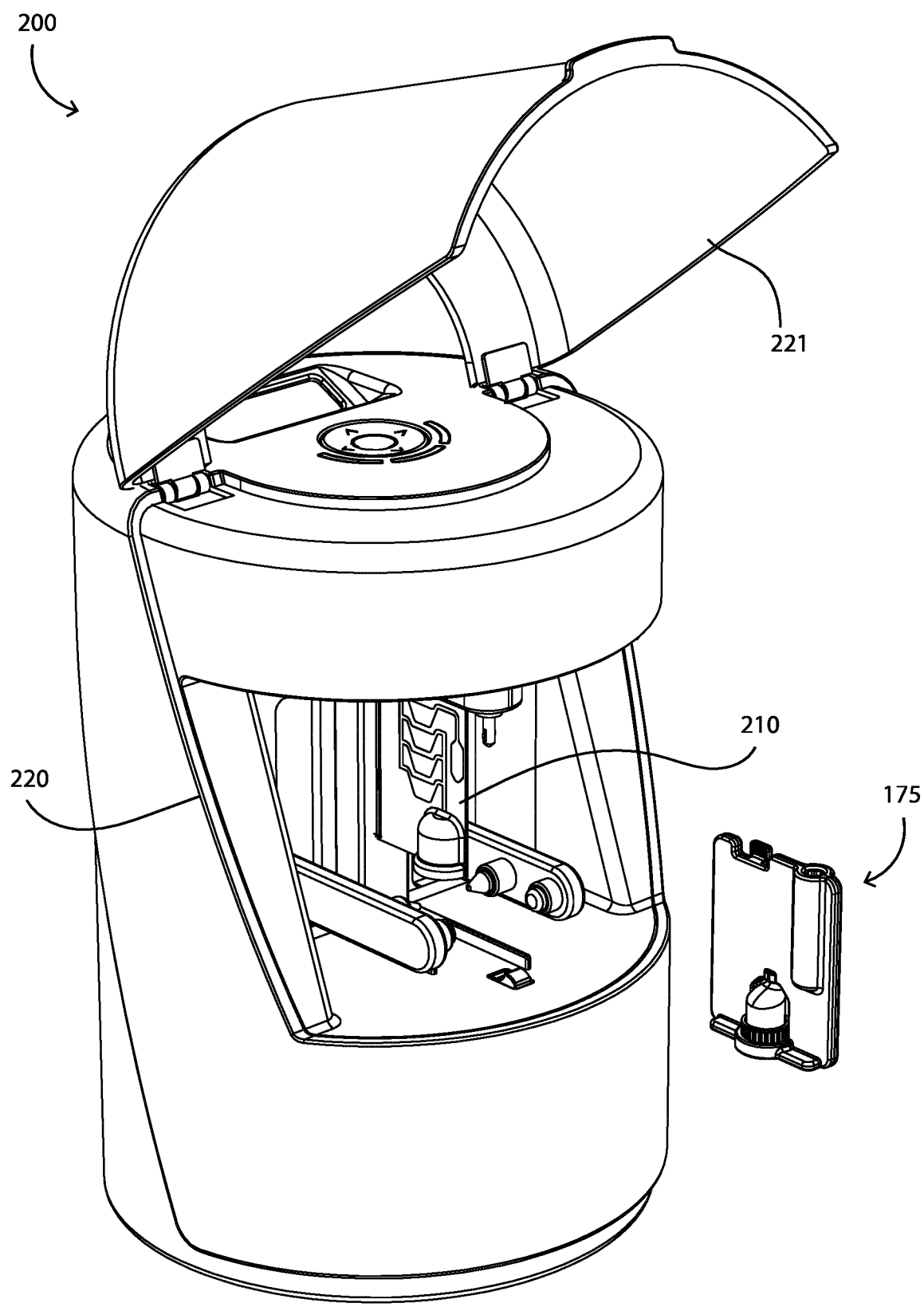
Figure 11:
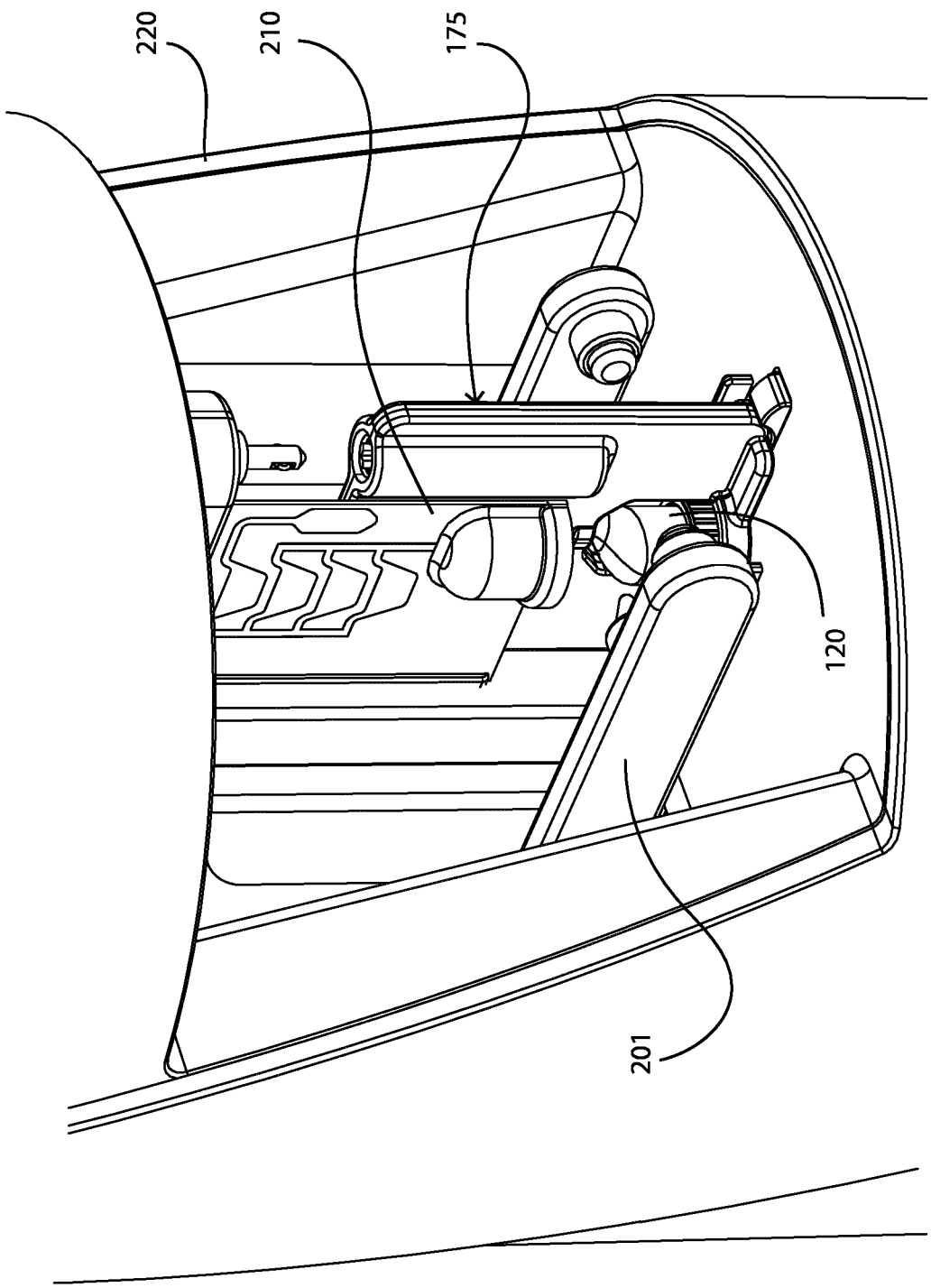
Figure 12:
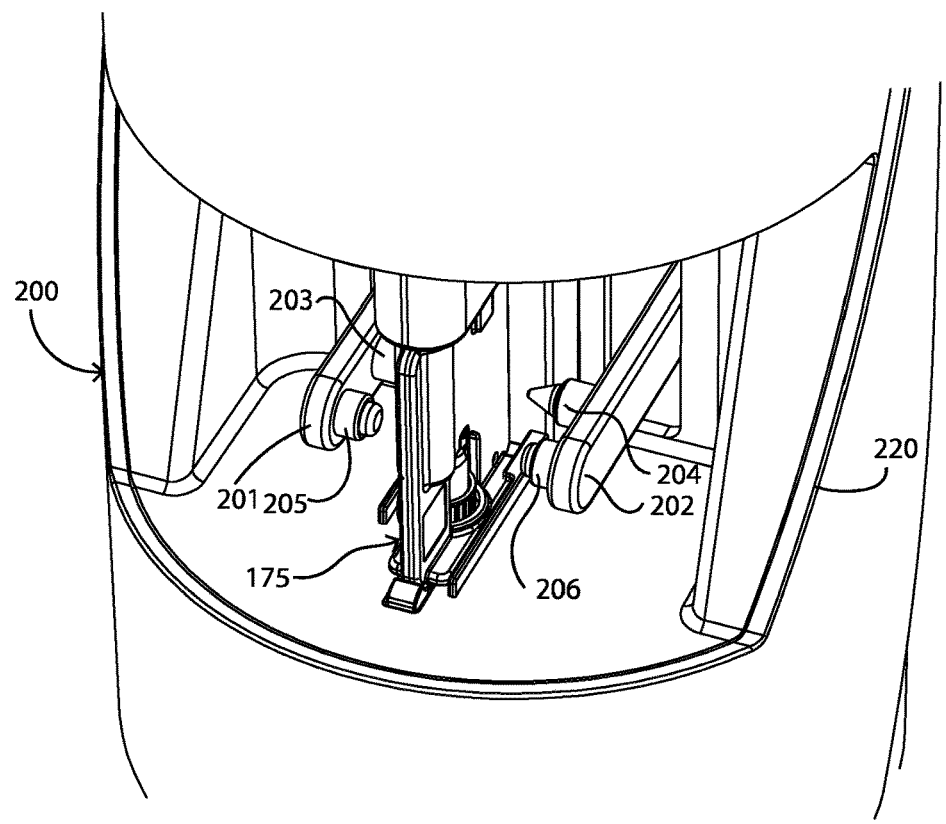
Figure 13:
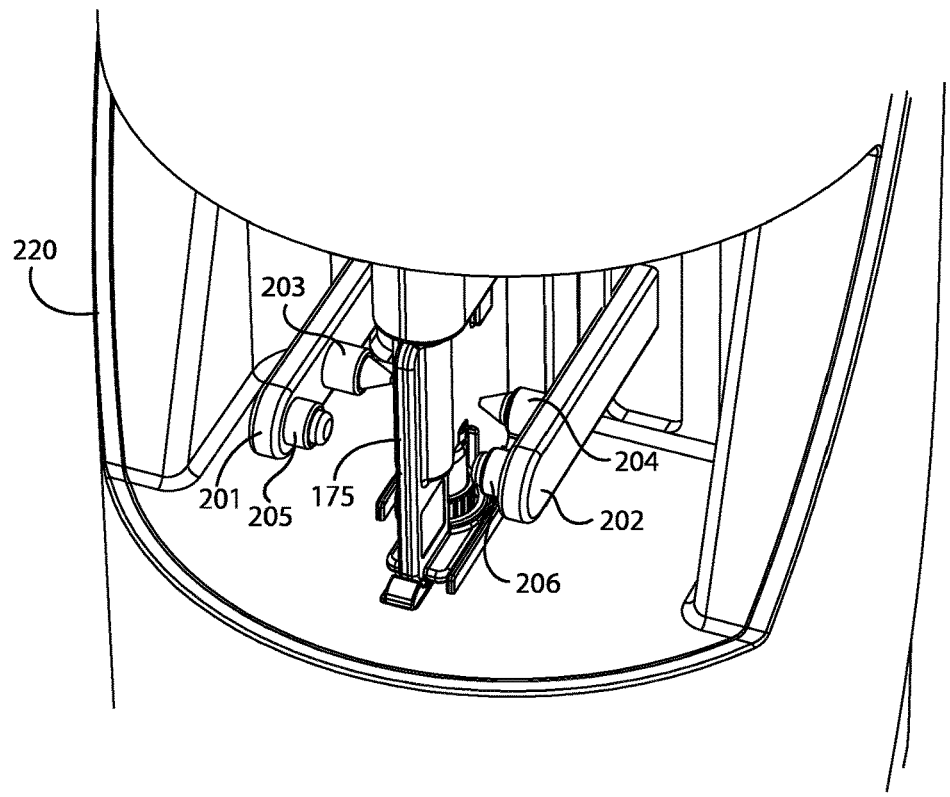
Figure 14:
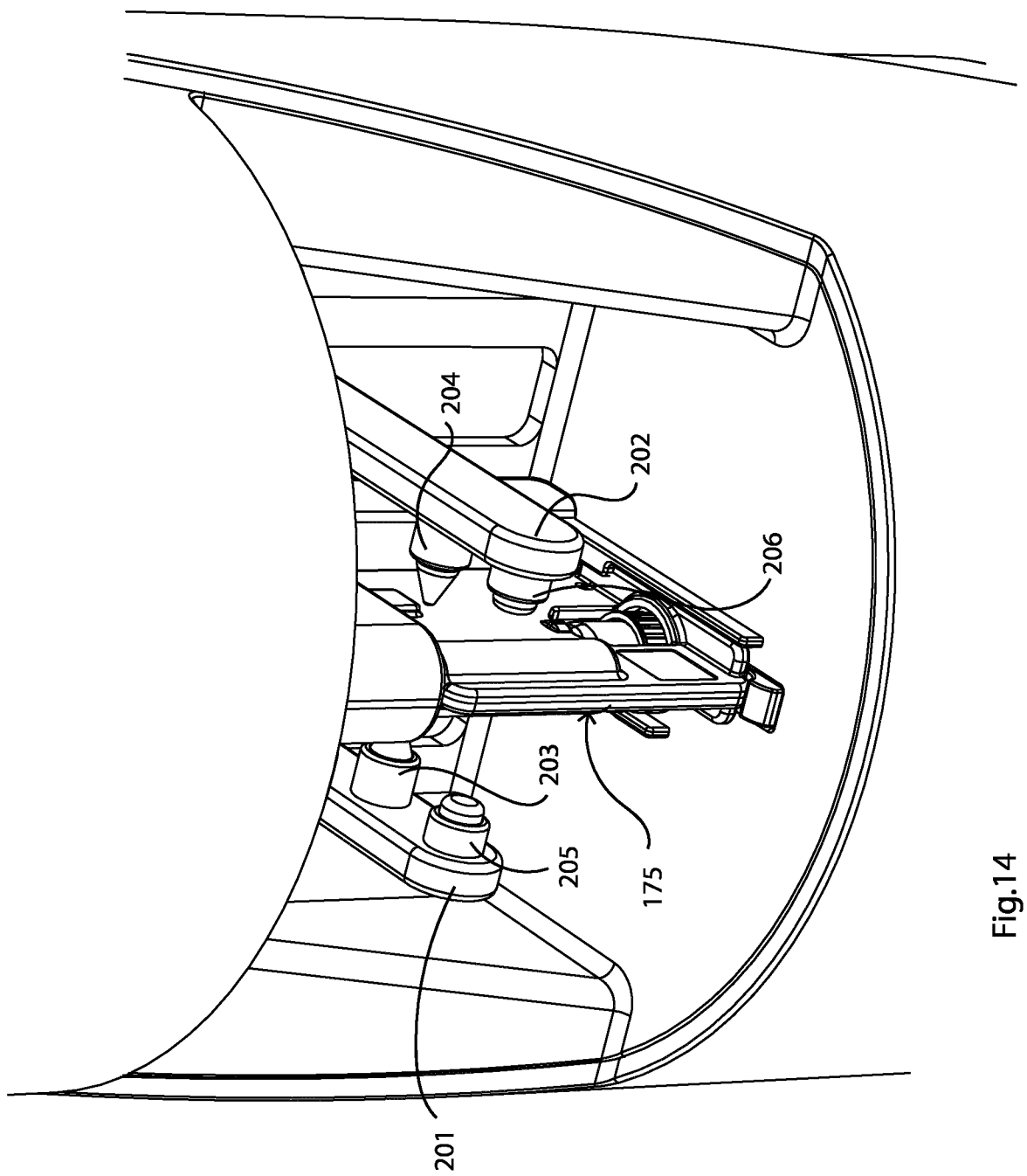
Figure 15:
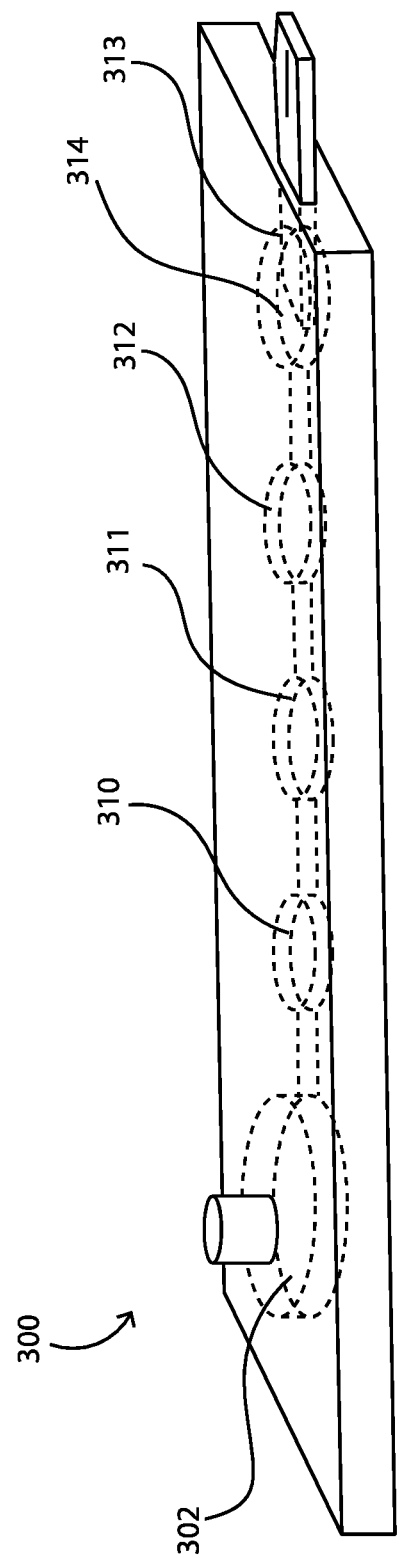
Figure 16:
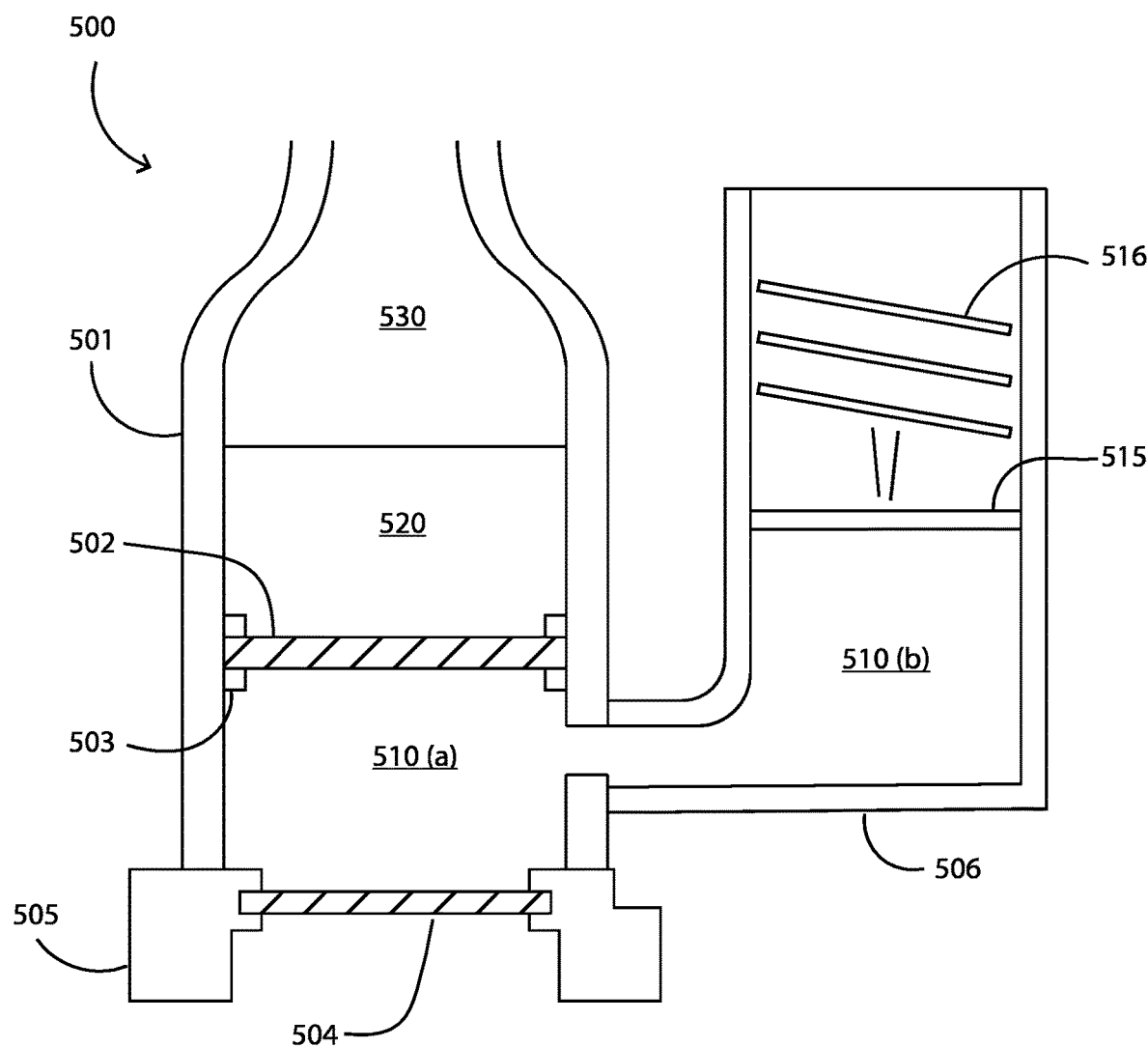
Figure 17:
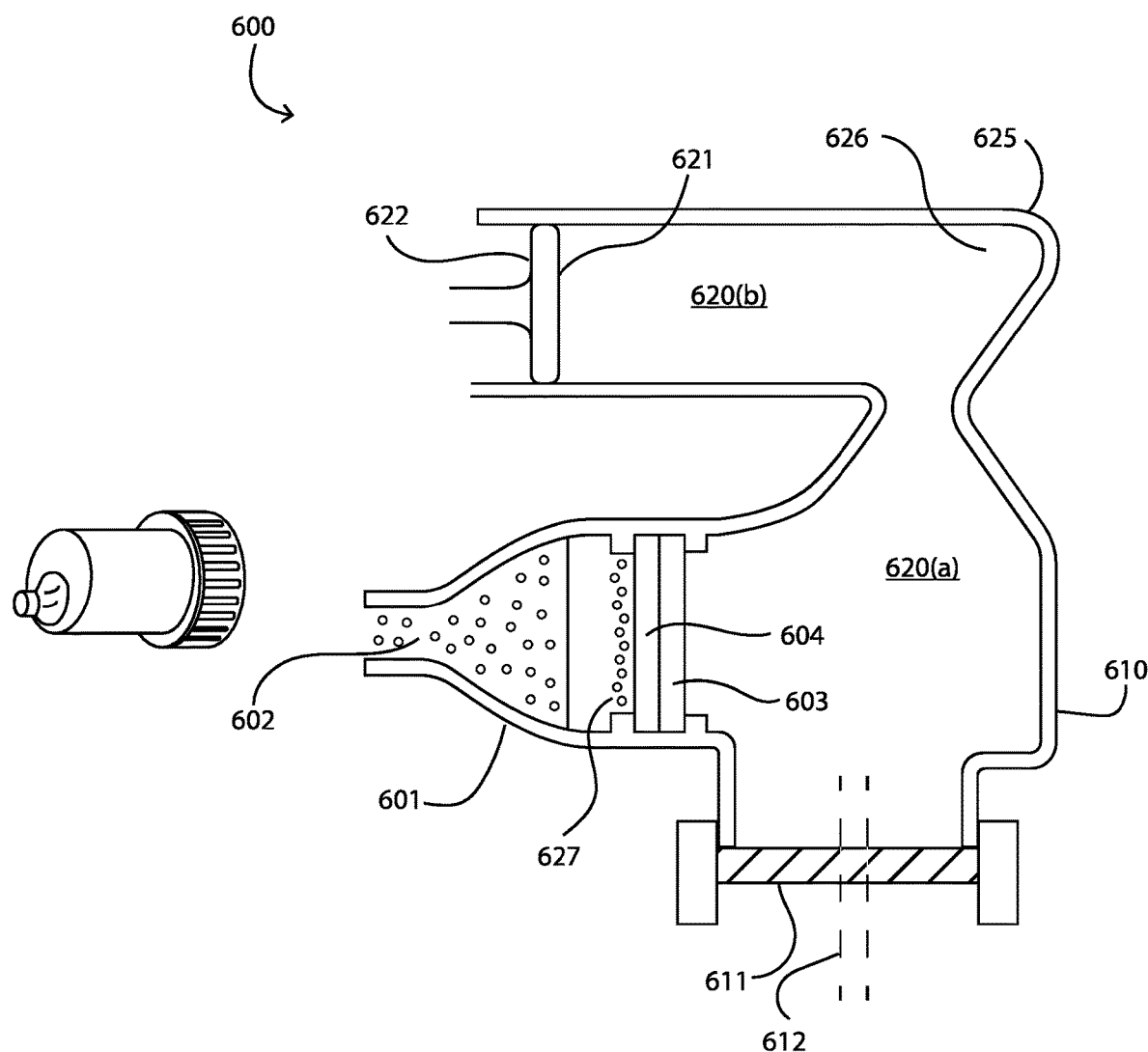
Figure 18:
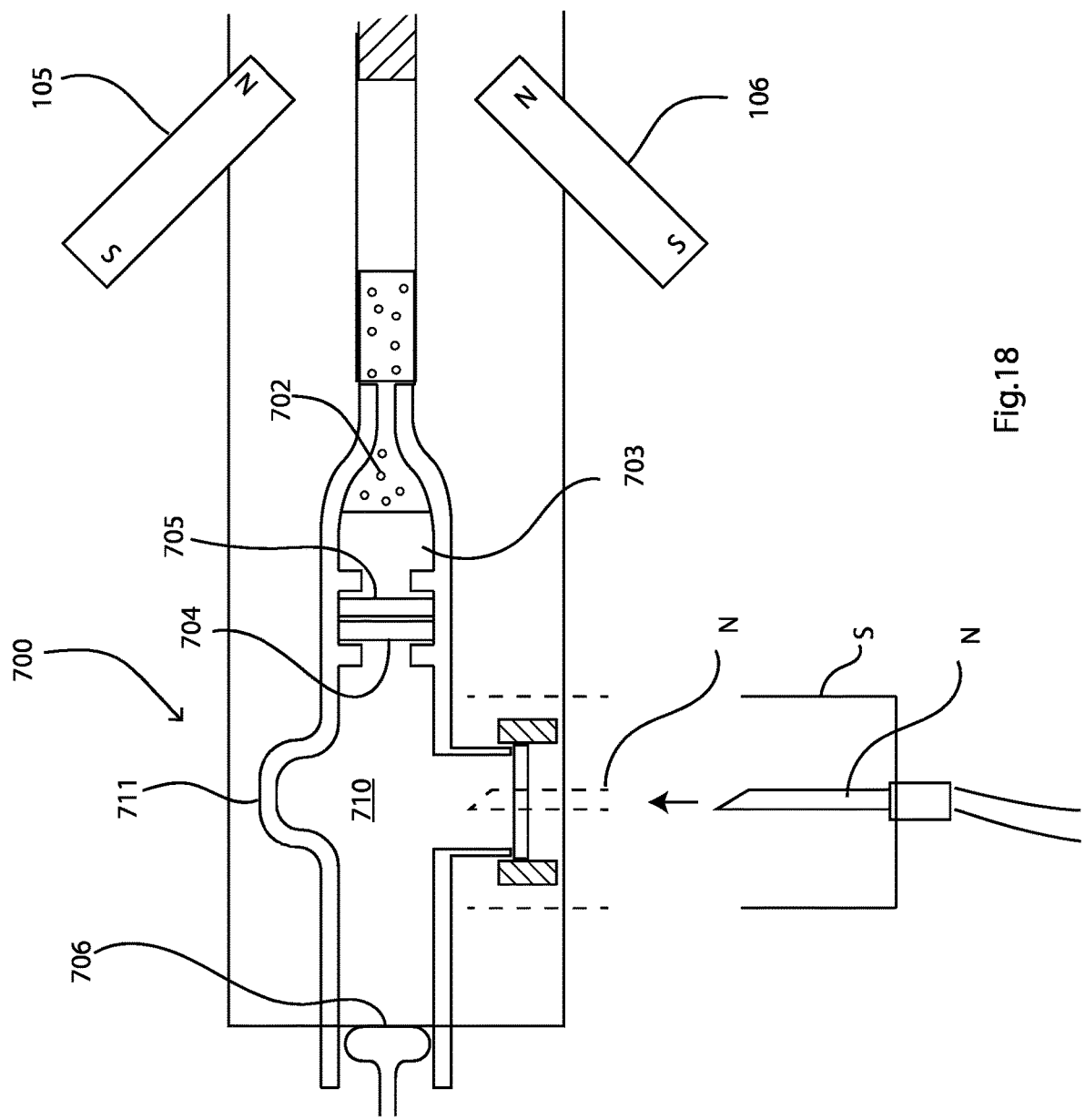
Figure 19:
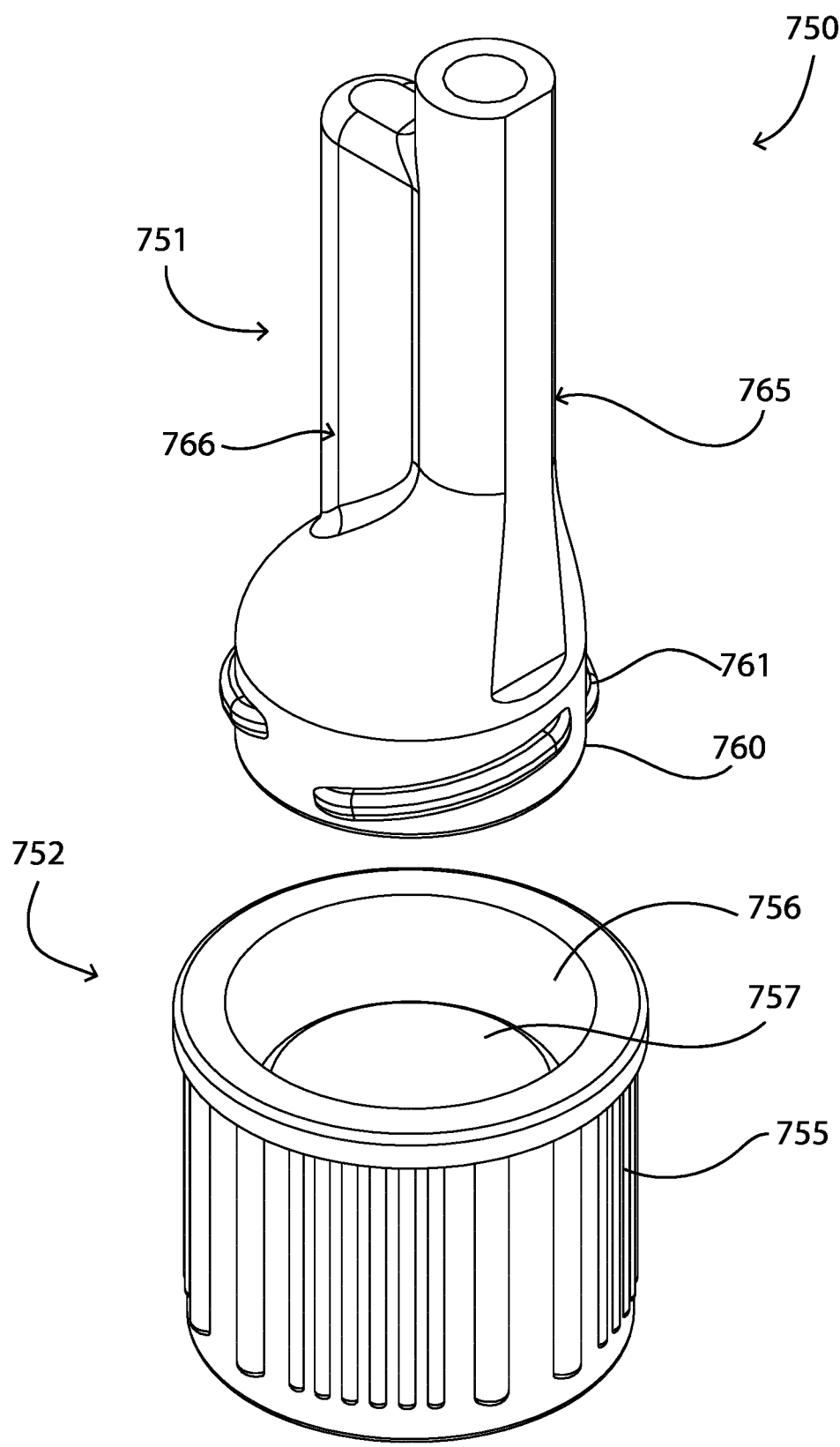

FIGS. 9(a) and 9(b) show the effect of a hydrophobic coating on a channel for shape of an oil-water interface;

FIG. 10 illustrates the cartridge being inserted into an automated portable diagnostic reader of a system of the invention;

FIGS. 11 to 14 show the cartridge in the reader during use;

FIG. 15 shows an alternative device;

FIGS. 16 to 18 are diagrams showing inlet stages of cartridges of other embodiments;

FIG. 19 is a perspective exploded view of an alternative inlet, and

Figure 20A:
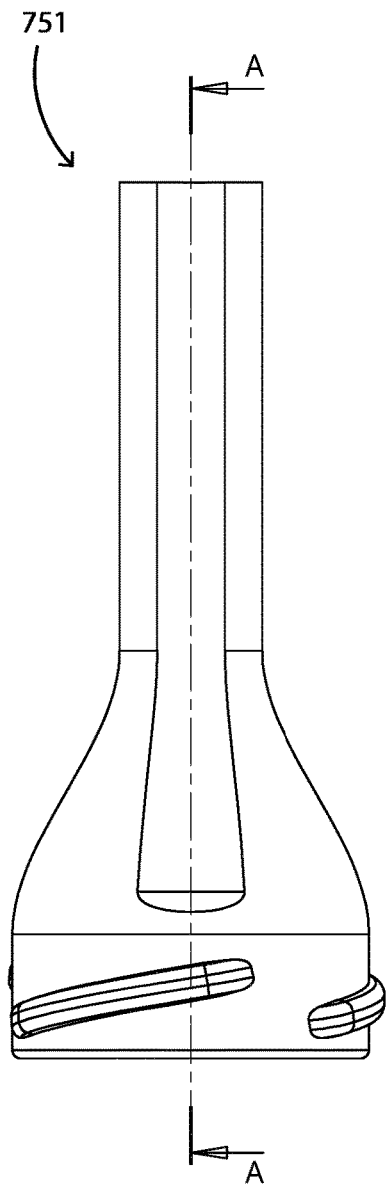
Figure 20B:
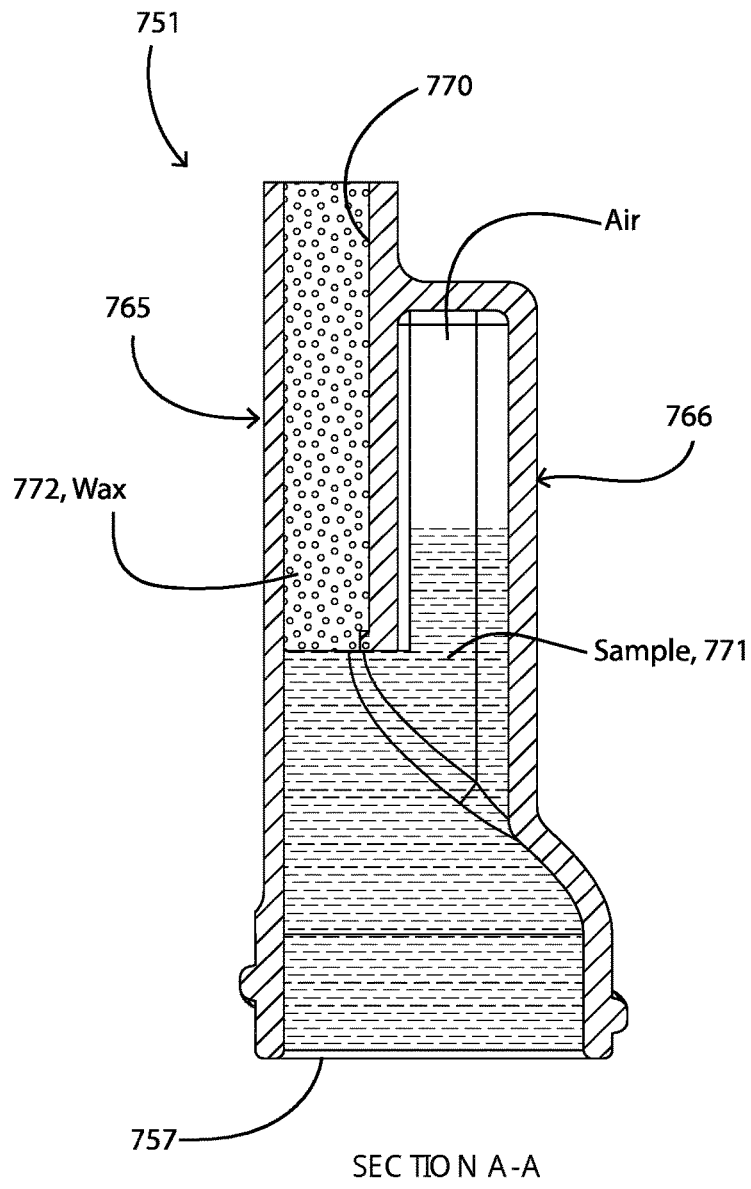

FIG. 20(a) is a side view of the main body of the inlet, and FIG. 20(b) is a cross-sectional view showing it in use.

DESCRIPTION OF THE EMBODIMENTS

Overview

A diagnostic device is in the form of a cartridge for inserting in a reader which provides for movement and heating of analyte, the reader and the cartridge providing together a diagnostic system. The system is such that the disposable cartridge which has a processor, controls the reader unit, simplifying the reader unit and maintenance thereof.

It is also envisaged that a device may be used to complete an assay without an automated actuation system, with analyte movement and/or heating being performed manually by a skilled operator. However, a reader linked with the sensor would be required wither as part of the device or separately.

The device is in one example for taking a sample of blood, lysing the sample to release an analyte such as DNA, RNA, proteins, or extracellular vesicles, and tagging the analyte to magnetic transport beads (T-beads). In other examples, the sample is processed or lysed beforehand.

The whole blood sample may have a suitable diluent added, such as DI. Hereafter, blood sample is taken to mean either a whole blood sample or diluted whole blood sample.

In one example, a covalently-attached PNA (peptide nucleic acid) Probe1 on a T-bead captures an RNA (Ribonucleic nucleic acid) target. This is achieved by transport beads ("T-beads") magnetically moving the analyte through a series of assay stages within the device. An external magnetic field is applied to the device so that the T-beads move magnetically and sufficiently treat the analyte so that a diagnostic reading can be taken of the analyte.

Figure 1:
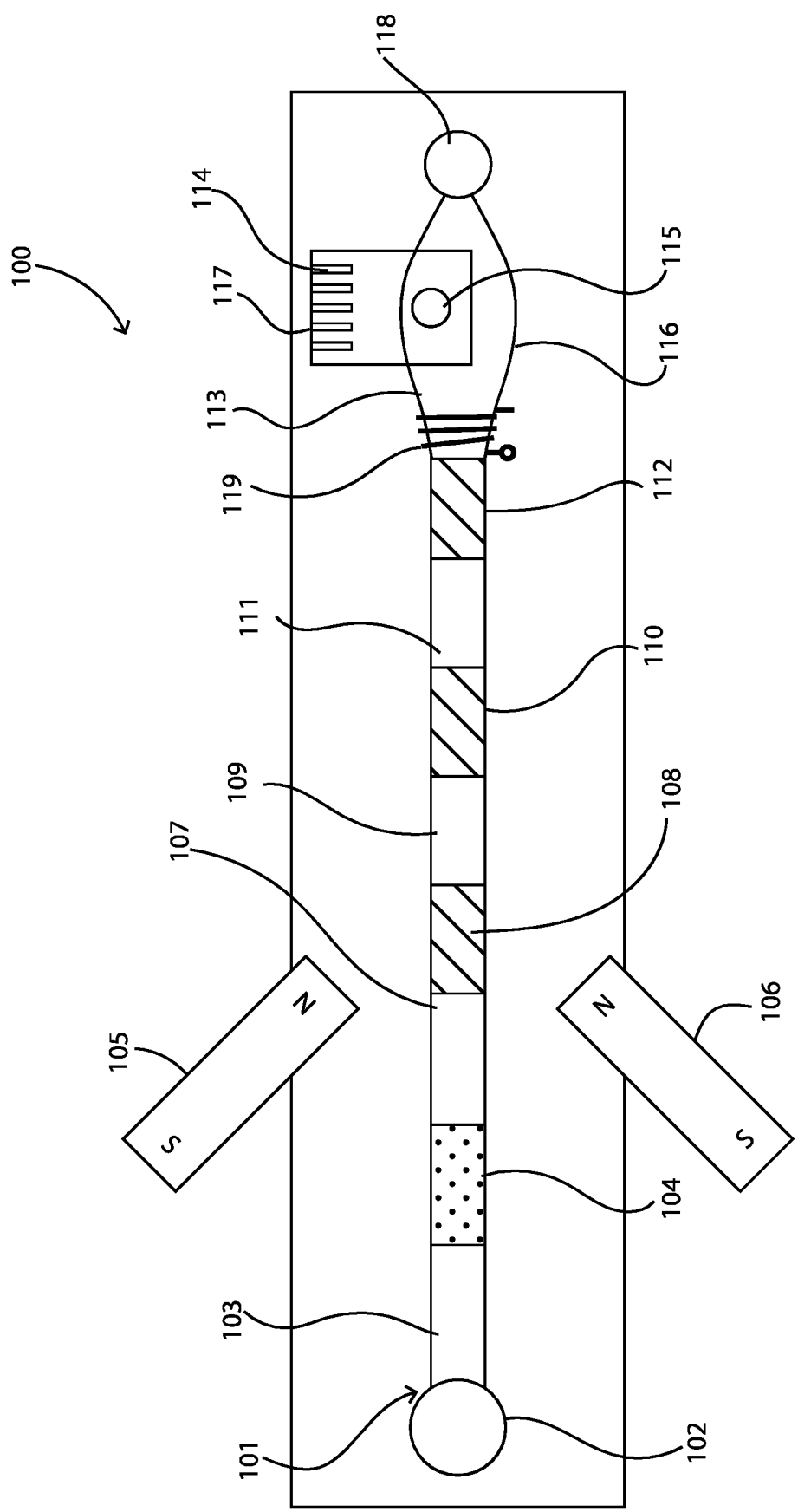
FIG. 1 is a diagrammatic plan view of a diagnostic device.

Referring to FIG. 1 a device 100 of one embodiment is illustrated. The following are the components 101 plastic assay tube having an internal diameter of 0.6 mm (more generally preferably in the range of 0.5 mm to 1.0 mm)
102 blood inlet,
103 lysis chamber,
104 solid wax and bead matrix plug,
105, 106 dipolar magnets,
107 first wash chamber,
108 first oil barrier, (166)
109 PNA Probe2 attachment chamber,
110 second oil barrier,
111 second wash chamber,
112 third oil barrier,
113 sensing chamber,
114 contact pads or fingers, in this case gold-plated,
115 capacitance sensor on the chip 114,
116 microfluidic capsule,
117 CMOS chip,
118 removable rubber plug, and
119 induction coil heater.

In more detail, the device comprises a simple microfluidic tube (101) with a series of assay stages including the lysis buffer 103, the aqueous wash buffers 107 ad 111, and oil/wax barriers 108, 110 and 112 through which the magnetic beads travel.

Inlet and Lysing

A hot plate underneath the device is used to assist lysis of the whole blood and/or any viral envelopes or capsids present in the sample. This act of heating the lysis section also melts the wax and bead matrix plug 104. This wax/bead matrix contains magnetic beads ("transport beads" or "T-beads") of ~1 µm in diameter. The beads have a coating such as a covalently-attached PNA probe(s), selected for capturing a specific target NA analyte. Please refer to FIG. 2, in which the attachment of Probe1 to a T-bead is shown, with two strands of captured NA shown.

The device is in one example for taking a sample of blood, lysing the sample to release an analyte such as DNA, RNA, proteins, or extracellular vesicles, and tagging the analyte to magnetic transport beads (T-beads). A covalently-attached PNA (peptide nucleic acid) Probe1 on a T-bead captures an RNA target. This is achieved by transport beads ("T-beads") magnetically moving the analyte through the series of assay stages within the device 100. An external magnetic field is applied to the device by the magnets 105 and 106 so that the T-beads move magnetically and sufficiently treat the analyte so that a diagnostic reading can be taken of the analyte.

It will be appreciated that the application of an external magnetic field collects the T-beads, and causes them to break through the interfacial tension between aqueous lysate and a now molten wax layer. It is preferred that at least one of the magnets is a conical focal magnet, for optimum control.

A small volume, for example in the range of 10 µl to 20 µl, of whole blood is applied to the inlet 102 (directly or using a pipette). A small plug is placed over the inlet 102 to seal the device. A lysis buffer in the tube segment 103 mixes with the blood, causing lysis to occur.

In another embodiment, the PNA and T-beads are micro-encapsulated (e.g. ethyl cellulose, polyvinyl alcohol, gelatin, sodium alginate) prior to being incorporated in the wax. This may provide for better stability and controlled release of the particles during the assay.

Figure 2A:
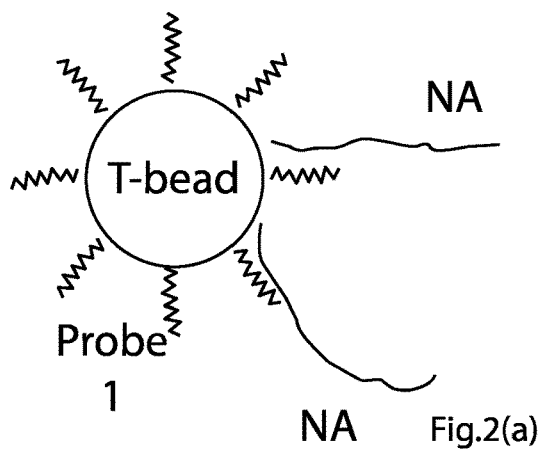
FIG. 2(a) is a diagram illustrating a transport bead (T-bead) and its probe.
Figure 2B:
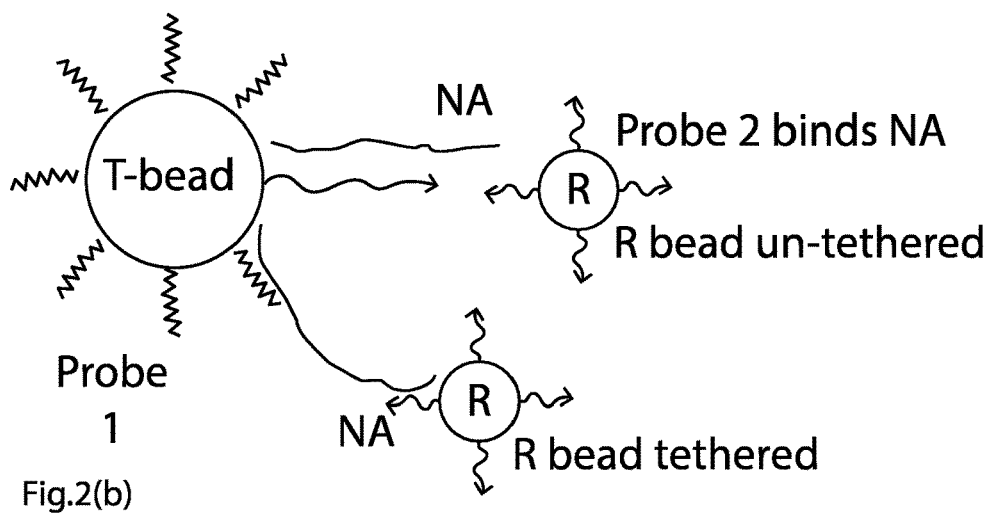
FIG. 2(b) shows it binding to a reporter bead (R-bead)

Once the wax plug is melted the beads are pulled magnetically by the two opposing external magnets 105 and 106 (either manually or robotically-operated) towards the left as shown in FIG. 1 into the now-lysed blood in the lysis reservoir 103. The covalently-attached PNA probes on the surface of the magnetic T-beads hybridises to and captures target NA within the lysate, as shown in FIG. 2. Small circular movements of the external magnets on either side of the tube promotes active mixing and increased binding and capture efficiency by the beads. Thus, a target NA becomes attached to Probe1 which in turn is covalently attached to the T-bead.

The magnets may be bar or disc shaped, or also may be conical in shape, and it has been found that this shape is very suitable for accurate manipulation of the magnetic beads in channels, as the field lines are concentrated at the magnet apex. This can concentrate the beads within the channel into a small area, move them effectively against interfacial tensions between aqueous solutions and wax separation plugs or oil within the cartridge, so that they 'walk' through the assay steps of enrichment, purification, washing, tethering, and sensing, under magnetic control.

The use of two opposing magnets, 104 and 105, greatly assists bead movement, mixing, and dispersal, by creating a steep gradient in the magnetic field and particle repulsion between the two opposing North poles. This mixing and homogenising of the beads within an aqueous solution provides excellent assay kinetics, and good overall assay time. The steepest magnetic gradient point is achieved by moving the two magnets away from the channel, to a distance of approximately 6 mm to 12 mm. Both magnets may be moved simultaneously or one magnet may be moved at one time. Rotating or oscillating one magnet back and forth against the other static magnet also effects good mixing.

In one embodiment the lysis buffer can be adjusted so as to only cause lysis in certain target cells or capsids in the sample. This adjustment may for example involve a drug designed to bind to a particular protein target on the viral surface which damages membrane integrity.

In one embodiment, the probe also contains cell-penetrating peptides (e.g. trans-activating transcriptional activator TAT) to facilitate cellular uptake prior to lysis. This limits exposure of the NA target to nucleases prior to lysis. This would be particularly beneficial in the case of PNA probes wherein nucleases do not recognise the PNA-NA duplex. The probes could be bound to particles or biotinylated for capture by streptavidin-coated beads.

In one embodiment the hot plate can be adjusted to specific temperatures so as to only cause lysis of certain types of cells or capsids in the sample. In one example, the stress induced by such a temperature adjustment may cause white blood cells (containing DNA) to respond, preventing their lysis, whereas other cells and, particularly, viral particles which cannot respond to these temperature variations are lysed. This is advantageous where the white blood cells contain retroviral DNA which can confound an assay for retroviral RNA. This retroviral DNA will not be available within the lysate produced here.

The T-beads with attached NA target are now magnetically aggregated using the external magnets and pulled back though the melted wax plug (104). This wax acts as a barrier which separates the biological sample from the rest of the assay. As the beads pass into the wax they interfacial tension and entropy causes them to form into a tight, aqueous ball of beads (~0.5 mm diameter), thereby, limiting the amount of non-targeted biological contaminants. This ball of beads moves easily in the oil/wax and control of its movement (including around obstacles) is facile.

Lysis Vessel

In another embodiment, a lysate vessel (100 µl-1 ml) can be affixed to the end of the assay tube to provide a lysate stage instead of the tube segment 103. This lyses the sample, for example as described in WO2015086652, for example by heating at a temperature in the range of 60° C. to 99.5° C. for a time duration in the range of approximately 2 to 5 minutes.

Figure 3:
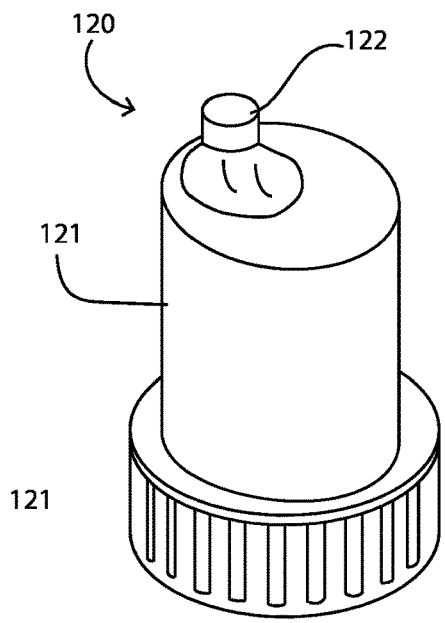
FIG. 3 shows a an inlet lysate vessel of a device of another embodiment.

Referring to FIG. 3 such a lysate vessel 120 may have a main body 121 and a funnel-shaped outlet 122 which retains a solid plug of wax, and this must be melted by the heater to allow passage of lysate into the first stage within the conduit. First probe attachment may occur in this chamber. A sample can be introduced using a needle or capillary through a self-sealing rubber membrane such as a screw on Vacuette cap (167) or a built-in membrane. The inlet is designed to allow use of a simple safety device such as a vacutainer needle holder.

The lysing agent may be a surfactant such as Tween 20 or Triton X, a fatty acid such as Linoleic acid, a redox reagent such as dithiothreitol (DTT), a chaotropic agent such as guanidine thiocyanate, or an osmotic stress solution.

In one embodiment a lysing agent is stored in solution within the lysis chamber. In one embodiment a lysing agent is dried or emulsified onto the internal wall of the lysis chamber with a diluent stored separately in a pouch, which may be pierced and released by a needle or capillary during introduction of the sample.

First Wash Stage

Using the external magnets 105 and 106, the T-beads, with concentrated and enriched NA attached are pulled into the aqueous wash reservoir 107. Here, the T-beads are actively mixed using the external magnets to release any non-target biological material which may have been carried thought the wax barrier. The T-beads are then once again aggregated and pulled through the first oil phase 108.

The main purpose of the wash stages is to decrease contaminants from an aqueous envelope which typically forms around the beads as they are magnetically transported. They cause the envelope to disperse out in solution and any contaminants to thereby disassociate from around the beads.

Reporter Probe Attachment Stage

Once washing of the analyte has been completed, the magnets 105 and 106 move the washed T-beads to the next assay stage, through the first oil barrier 108 into the reservoir 109. This oil can be a low-viscosity oil such as silicone through which the beads can particularly easily travel. The reservoir 109 contains a PNA probe (Probe2) which is complementary to a different section of the target NA than the original Probe1. In this embodiment the reporter Probe2 is covalently attached to a reporter bead (R-bead).

These R-beads are significantly less magnetically susceptible than the T-beads, either by being much smaller in diameter than the T-beads (0.1 µm to 0.5 µm vs 1.0 µm) or containing fewer superparamagnetic nanoparticles for a given mass or may be made of a non-magnetic material.

The R-beads can be produced using a fluidic system to be doped with materials such as Titanium dioxide or Barium titanate to give a strong signal to a capacitance sensor. These can be produced using feedstocks of small nanoparticles (30-300 nm) of high dielectric constant such as barium titanate with a hydrophobic coating such as oleic acid. Fixed volumes of these emulsions of nanoparticles are fed into the microfluidic and can be mixed in precise ratios with feedstocks of other materials (including superparamagnetic ferrite nanoparticles). These mixtures of nanoparticles can in turn be enmeshed or encapsulated in a coating of silica or polystyrene for stability purposes, including ease of modification of the surface chemistry of these particles. It is easier to control the amount of high K dielectric material in these R-beads than to generate or commercially acquire monodisperse particles of the high K material. Tuning the R-beads in this fashion provides an excellent capacitance signal on the sensor.

Using the external magnets, T-beads are mixed within this reservoir. If any target NA is present on the T-beads they bind and become attached to PNA Probe2 on the R-beads. This binding of the two probes across the same NA results in the T-beads and R-beads being tethered together, as shown in FIG. 2. A T-bead-R-bead tethered sandwich is now formed, only if the NA target is present. The sandwich comprises: T-bead—Probe1—target NA—Probe2—R-bead.

T-beads are once again magnetically aggregated and removed from the reservoir 109 though the second oil barrier 110 and transported into the aqueous reservoir (e.g. DI) 111 which forms the second wash stage.

Figure 2C:
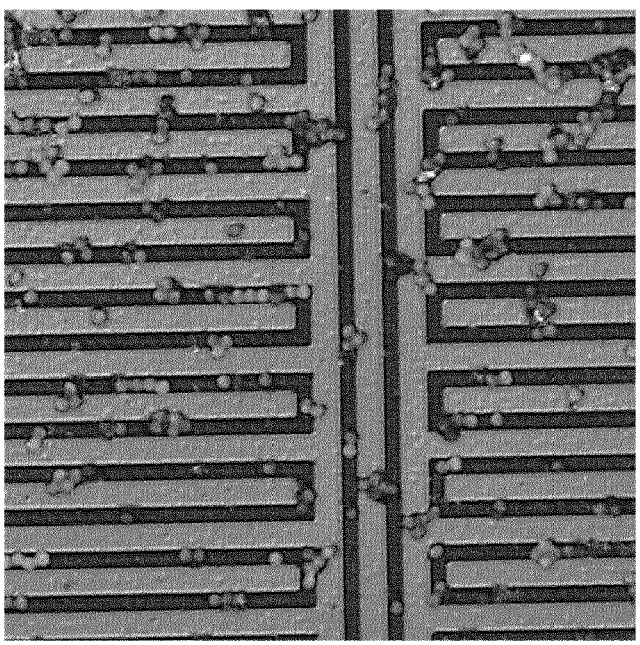
FIG. 2(c) is an SEM micrograph with a magnification of 2500 showing sensor electrodes of about 2 µm width and R-beads of about 1 µm diameter on and between the electrodes at the sensing stage.

For context and further illustration, FIG. 2(c) is a 2500-magnification SEM showing, in this case, 1 µm R beads after they have passed through the device and overlie the sensor device electrodes (rectangular array, 3 µm width).

In another embodiment Probe2 is biotinylated so that a positive capture result can be observed through capture of Streptavidin conjugated horseradish peroxidase. Using a similar liquid-liquid purification process, when these are selectively transported and provided with the substrate Tetramethylbenzidine (TMB), a colorimetric change is observed indicating the presence of target NA (e.g. HIV).

In one embodiment Probe2 has a fluorescent moiety or particle attached which can be detected using a plate reader etc.

Second Wash Step

Once the T-beads have been moved into the reservoir 111 by the external magnets, the beads are once again mixed and separated into solution, this time to release any non-attached R-bead which may have been carried through from the previous capture phase. The T-beads are then aggregated once again and pulled through the oil barrier 112 into another reservoir 113 which includes a semi-conductor sensor 115 on a chip 114. There is now a 1:1 ratio of R-beads to NA targets. This is because the R-beads can only get from the reservoir 111 to the reservoir 113 if tethered to the T-bead by the Probe1—target NA—Probe2 sandwich.

The T-beads are now magnetically moved over the surface of the sensor 115. Heat is applied in order to melt the PNA-Probe2-NA links and separate the R-beads from the analyte NA and hence separate the T-beads. The magnetic T-bead can now be pulled away, leaving the much less magnetic (or non-magnetic) R-beads over the sensor surface. The T-beads are moved back through the oil barrier 112 as they are now no longer required, and should they remain in the reservoir 113 may affect the capacitance reading on the semi-conductor chip.

The Probe2 heating temperature to separate the second probes is typically 60° C. to 85° C., or it may more generally be in the range of 50° C. to 100° C. depending on its exact hybridization sequence. This temperature may be achieved by placing the device substrate on a hot plate, and/or or by using an induction coil 119, which enables magnetic induction heating of ferrite R-beads, as described in U.S. Pat. No. 5,378,879.

The T-Bead—RNA—R-Bead sandwich may also be broken chemically, by direct destruction of the nucleic acid, for example, by using a 10 mMolar solution of Potassium (or other) hydroxide at a temperature of 80° to 95° C.

In one embodiment the reservoir 113 is filled with ethanol. Attached to the reservoir is a Fluorosilicone (or other ethanol resistant material) plug 118 which when removed allows the ethanol within to evaporate.

Multiplexing

It will be understood that multiple NA targets could be targeted in parallel using the above approach, e.g. for detecting two types of virus at the same time (HIV_T-bead—HIV_Probe1—HIV_Target NA—HIV_Probe2—HIV_R-bead; HCV_T-bead—HCV_Probe1—HCV_Target NA—HCV_Probe2—HCV_R-bead). This results in two types of R-beads arriving on the sensor. The sensor can determine the quantities of each type of R-bead.

The sensor may have at least two sensor regions with PNA probes which are complementary to PNAs on the R-beads so that each type of R-bead becomes hybridised to the correct sensor. The PNA probes on the sensor may be complementary to the HIV_Probe2 and HCV_Probe2.

Alternatively, the PNA probes on the sensor may be complementary to a standard PNA probe on each type of R-bead. These R-beads would then be additionally functionalised with HIV_Probe2 or HCV_Probe2. As the sensors come manufactured with standard PNAs, this approach allows more rapid assay development. Ideally, the standard PNAs should be designed to have no interaction with NAs found in nature and have good robustness to chemical and heat treatments found during wafer-level manufacture (e.g. through careful design of the sequences).

Sensing Stage

The sensor is in one embodiment a monolithic IC with a multi-layer internal circuit connected to pads for communication of data and receiving power and to sensors such as capacitive electrodes, all integrated from a fabrication process. The sensor chip 114 is in this example a CMOS semiconductor capacitance sensor chip and is mounted in the encapsulated microfluidic structure at the end of the assay tube 101. It contains a high-resolution sigma-delta capacitance-to-digital converter, calibration memory, and digital processing circuitry, including I2C serial communication. A protrusion 117 with four gold fingers (VDD, GND, Sclk, SDa) connect the chip to an external reader or computer. A variety of methods are known for packaging of CMOS chips in microfluidics (Datta-Chaudhuri et al. 2014 Lab Chip, 14, 1753 and references therein) including wire-bonding; PCBs, UV polymers; through chip vias and use of liquid metals to make electrical connections and seal the chip in the microfluidic. In such microfluidic developments the electrical connection to the sensor chip 117 is an issue as it is a requirement to seal the microfluidic channel to the chip 117, this process may cause damage to bond wire connections or require globbing with materials that may be incompatible with some reagents. By designing the sensor chip 117 to extend the connections away from the sensor area, the outside connection is simplified to allow the use of an Elastomeric connector (e.g. Zebra® strip), or Anisotropic adhesive (e.g. 3M 9703) to connect the chip to a protruding connector.

In one embodiment, the elastomeric connection forms a gasket or microfluidic wall around the sensor area. Overmolded or elastomeric parts are often built into microfluidic components for the purpose of forming good seals between hard silicon and harder polymeric materials. By using an elastomeric connection (which is usually a silicone matrix containing conductive material such as carbon) this one component or layer of material solves two problems, namely electrical connections and microfluidic sealing, making assembly of the cartridge simpler and cheaper.

Figure 4:
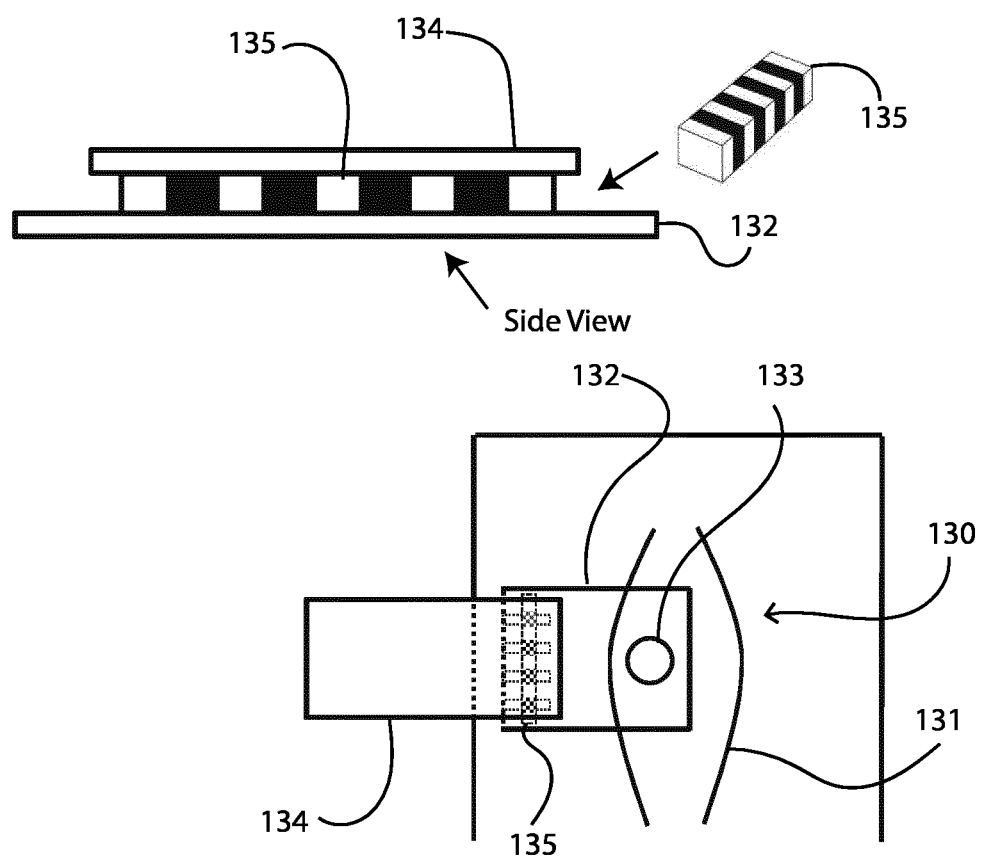
FIG. 4 is a pair of diagrams showing a sensor of a device of another embodiment and how it connects to a socket of the reader.

FIG. 4 shows an arrangement, in which a sensor 130 has a sensor IC 132 with a sensing region 133 and which is connected to an interposer 134 via a "Zebra®" connector 135. This allows it to connect to a socket in a reader in a convenient manner. The connection to the interposer may be by soldering or any other suitable mechanical or solder or composite method.

A first "wet-capacitance" reading is taken by the sensor chip, of the R-beads in liquid. This provides a baseline reference calibration capacitance. After the liquid evaporates, a second "dry capacitance" reading is taken of the R-bead capacitance. Due to their dielectric constant being higher than air, any R-beads on the sensor surface give a capacitive signal, e.g. 1 fF (delta capacitance versus dry air) for 200 beads.

In simple embodiments, interdigitated electrodes on the sensor can be arranged to act as a "snag trap" for R-beads. This may be accomplished by orienting them perpendicular to the flow of beads and controlling the pitch of the electrodes so that only the small R-beads can fit between them.

Also, it will be appreciated that the sensor capacitive signal represents the sample target NA, due to the 1:1 ratio of R-beads to target NA. This indicates a positive qualitative detection of the target NA. With suitable controls, this is clinically very significant as it provides a true or false indication of whether the sample being tested contains the target RNA virus.

The value of this capacitive reading corresponds to the number of R-beads on the sensor surface, which corresponds proportionately to the number of target RNAs in the original blood sample. This is indirect quantification of the number of copies of RNA per unit volume of the original sample, i.e. the assay is both qualitative and quantitative. This number of RNA copies (the "viral load") is also clinically very significant. It enables a physician to better diagnose a patient's precise health condition, and prescribe the correct treatment drug to a patient.

In another embodiment, addition of a drop of toluene degrades the polystyrene coating of the beads, deforming them, so the core constructed of a high capacitance material, lodges nearer to insulated electrodes giving a further increase in capacitive signal and assay sensitivity.

It will be appreciated that the application of an external magnetic field collects the T-beads, and a conical focal magnet may be used to allow the plug of beads to break through the interfacial tension between aqueous lysate and a now molten wax layer.

This device is very suitable for rapid assay development, for simple assays, using flat-plate heaters, and magnets for bead movement and control.

Viral Load Quantification

The following describes a range of approaches from a simple way to deal with the specific problem of retroviral DNA through to a more complicated way. They all provide a liquid sample which can be whole blood through to serum.

Some viral targets (e.g. retroviruses) incorporate themselves as DNA in human cells. To distinguish such nucleic acid targets from cell free RNA within virions, the assay may also rely on the higher melting temperature of RNA-PNA, compared to DNA-PNA. This can be several degrees higher depending on sequence and enables differential melting with suitable control of temperature, to assist separation of cell-free RNA.

Some embodiments may include fractionation of a whole blood sample. The simplest embodiment involves centrifugation of a tube of whole blood and application of the virus containing serum component to the inlet. In another embodiment, a filter which is selective for white blood cells (containing the retroviral DNA) is applied (Acrodisc® WBC Syringe Filter) is used and requires only gravity in a 10-15 min incubation step. The filtrate containing only the viral particles, red blood cells, platelets produced is inputted to the device.

Alternative embodiments incorporate syringes with attached filter systems, in which the syringe may filter all blood cells to provide a serum sample for the device. U.S. Pat. Nos. 5,139,685 and 6,391,265 are two prior art examples of using a membrane filter in a device. In other embodiments, the blood passes through immunomagnetic beads suitable for removing certain fractions of the blood prior to application of the sample to the device (e.g. Whole Blood MicroBeads Miltenyi Biotec). The liquid sample can be added to the device with any suitable needle or pipette tip. In another embodiment, the sample can be applied by piercing a membrane seal 167 with any suitable sample-containing receptacle (e.g. syringe, needle, capillary, plastic dropper, pipette tip).

In another embodiment, in the inlet of the device the blood passes through a substrate or a bed of resinous beads which may be functionalised (e.g. Chelex) or coated in reagents to help prevent clotting (other chelating agents such as EDTA or citrate). In some embodiments, these beads could also be functionalised with ligands for selective capture of certain fractions of the blood after application of the sample to the device (following same principle of Whole Blood MicroBeads Miltenyi Biotec). In some embodiments, these beads are high density and gravity will hold these in situ, particularly where this section is vertical.

In other embodiments, the blood is lysed and the lysate passes through a static matrix of T-beads wherein the analyte is captured. In other embodiments, the lysate may be passed through a simple filter (<1.0 um pore size), built into the lysis vessel, which filters out aggregated material (lysed cellular membranes/protein) while allowing a filtrate containing an analyte (e.g. RNA) to pass. The analyte is captured on 1.0 um diameter T-beads, which cannot pass through the filter in the opposite direction. Passing blood through a built-in filter may require high back pressure to be/applied to the vessel. In another embodiment, the T-beads are held away from the aggregated material (e.g. by magnetic fields).

Automated Cartridge and Reader system (160)

Figure 5:
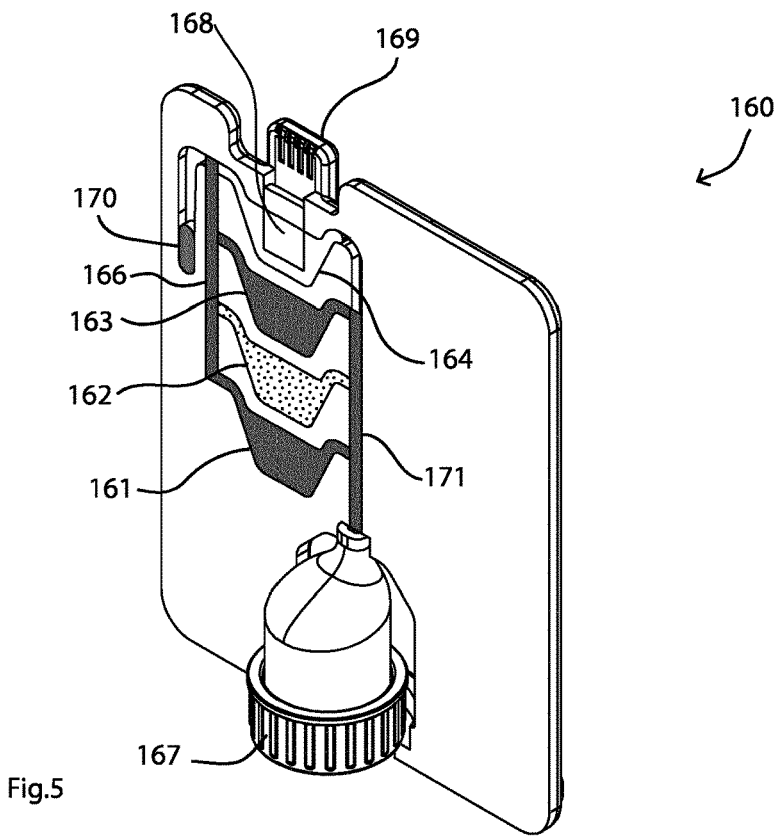
FIG. 5 is a perspective cut-away view of a device in the form of a cartridge for mounting vertically in a reader.
Figure 6:
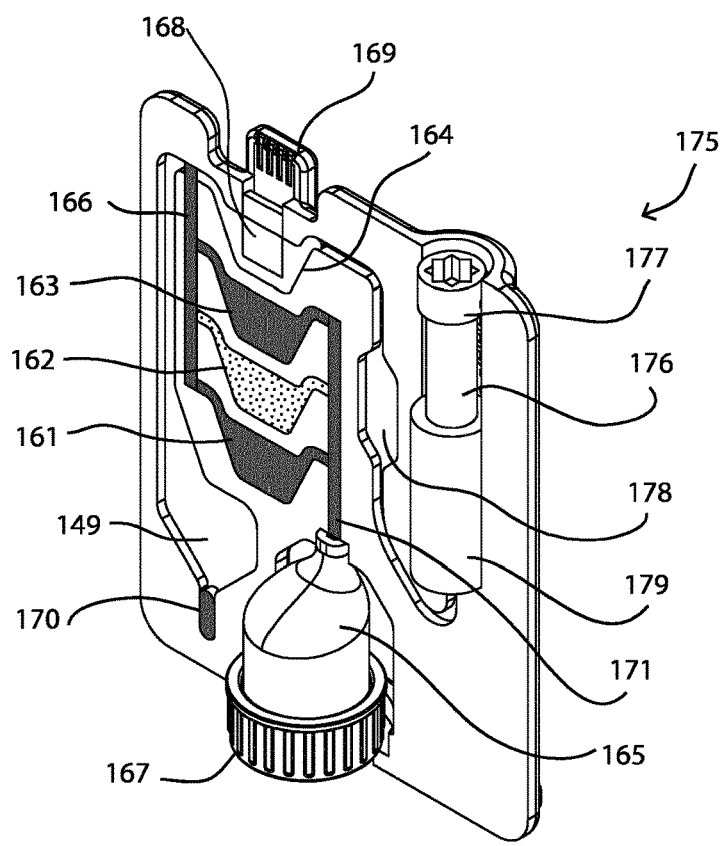
FIG. 6 is a perspective cut-away view.
Figure 7:
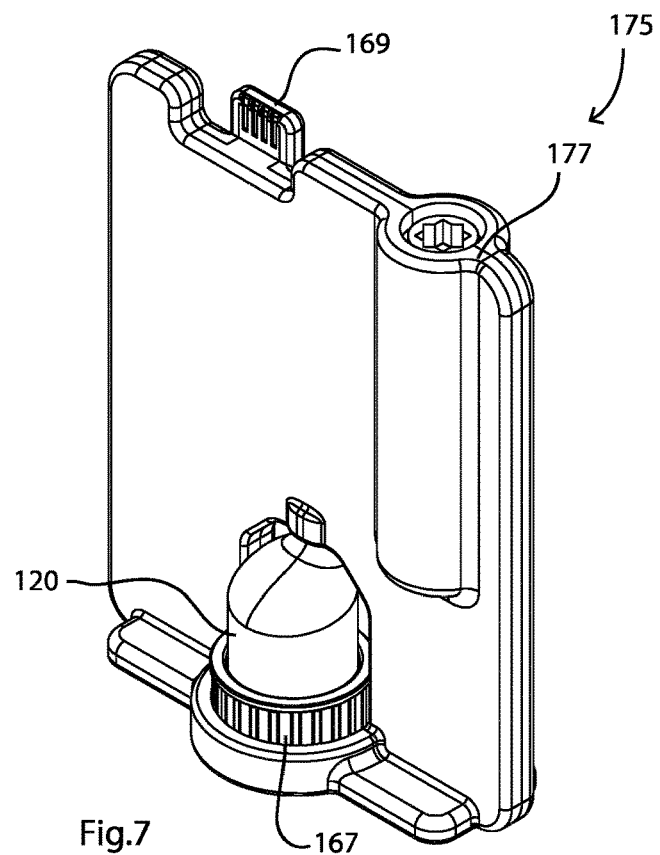
FIGS. 7 and 8 are front and rear perspective views of an alternative cartridge.
Figure 8:
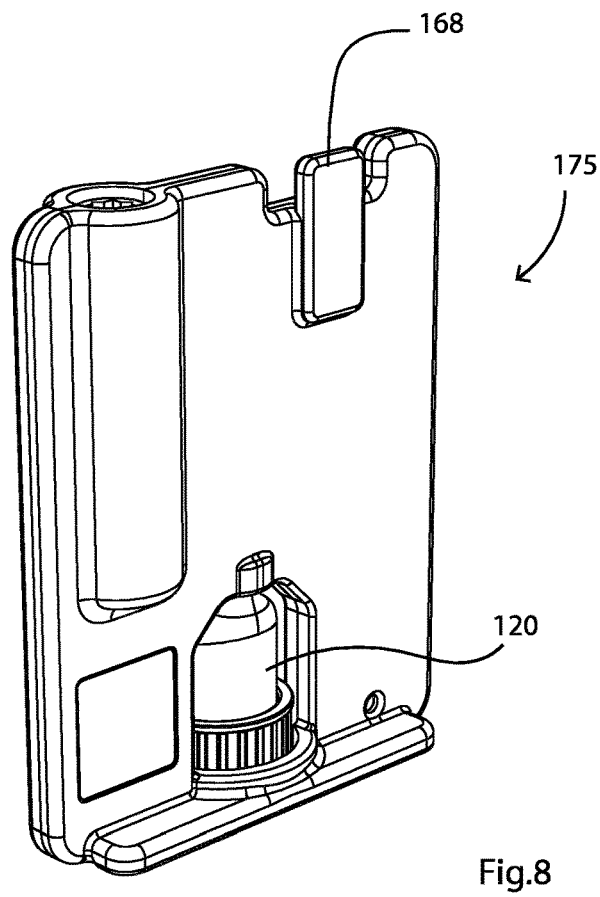

FIG. 5 shows a device 160 and FIGS. 6 to 8 show a device 175, which are two embodiments of injection-moulded fully integrated, sealed cartridges for insertion into a reader unit 200, as shown in FIGS. 9 to 14. Like parts of the two devices are indicated by the same reference numerals. Reservoirs 161, 162, 163, 164 are formed and joined by channels 166 and 171 through which the beads travel. The channels are vertical; they may be coated with Teflon™. Corners are rounded, to facilitate smooth bead movement. The microfluidic interfaces are designed with smooth, narrowed, vertical inlets and outlets to maintain the integrity of oil/water barriers across these even where the device is tilted. In summary the major parts are:

161 first wash chamber,
162 PNA Probe2 attachment chamber,
163 second wash chamber,
164 sensor stage
165 solid wax and bead matrix plug,
166 second and fourth wax/oil barrier,
167 blood inlet,

168 CMOS chip, and
169 contact pads or fingers, in this case gold-plated.
171 first and third wax/oil barrier.

The device 175 has the following additional components:
149 waste region,
170 air filter,
176 piston,
177 piston actuator,
178 wash buffer reservoir, and
179 gas expansion chamber.

In one embodiment the R-beads are suspended in an aqueous envelope within the wax/oil barrier (166) between the first wash phase (161) and the Probe2 attachment chamber (162). The T-beads are pulled into this envelope whilst moving through the barrier. With gentle magnetic manipulation the entire bolus of T-beads and R-beads can then be pulled into the Probe2 attachment chamber (162) where they can be actively mixed using the external magnets. The advantage of this approach is that it enables the T-beads to come into close proximity with the R-beads before incubation and also prevents R-beads settling out of solution in the chamber 162 and needing to be re-suspended.

As may be noted from the above, the device allows wax/oil barriers 166 and 171 to be used multiple times. These wax/oil barriers run along the sides of the aqueous wash and attachment chambers, connecting, but also isolating them at each aperture. This advantageously allows for a more compact design, simpler assembly and operation. To highlight this, the device 175 has two contiguous oil/wax areas (165/171 and 166) as opposed to the four such areas in the linear device 100 (104, 108, 110, 112).

There is a need for precise positioning of the cartridge to provide for mechanical movements and/or automation of the steps. This is referred to above in the design of the cartridge to be rigid with the design allowing for a system of locks to ensure precise positioning of the system relative to the reader.

In some embodiments, hydrophobic coatings (e.g. Aculon®) may be applied to surfaces of the microfluidic channels in 175 at the position of the interface of oil/wax and water to strengthen the barrier to aqueous solution.

As beads are pulled towards the oil/water meniscus (FIG. 9(*a*)) by a magnetic field applied to the bottom of the tube (as shown), it's noted in the bottom sketch of FIG. 9(*a*) that the beads will be deflected up by the shape of the meniscus at this point as the hydrophilic beads prefer to stay in the aqueous solution. As the beads move upwards away from the magnetic field, the strength of said field is reduced. This can make it more difficult for the beads to break the meniscus. In WO2015/086652A1, the magnetic field is applied through the centre of the oil/water meniscus meaning the gradient increases towards the centre of the meniscus, where it is easiest for the bolus of beads to collect and break through the meniscus. As shown in FIG. 9(*b*), in other embodiments, a hydrophobic coating 181 is applied to one wall 180 of the microfluidic at the location of the wax (or oil) 183. This changes the shape of the oil/water interface, as illustrated in FIG. 9(*b*) as water is repelled at that surface. As magnetic beads 182 approach, they encounter a smaller contact angle due to the hydrophobic coating 181. This changes the angle of incidence of the meniscus at the oil/water barrier, making it easier for the bolus of magnetic beads 182 to pass along the untreated microfluidic wall.

In preferred embodiments featuring the capacitance chip in the sensor, the chip needs to be carefully and mechanically inserted into the reader unit via a micro USB or other connection. In preferred embodiments, the cartridge is locked into the reader and the chip inserted vertically to provide for ease of access of the two robotic arms and heaters and a mechanical screw drive. Simple commercial point-of-care systems rely on passive flow systems such as capillary action and/or lateral flow strips. These have inherent weaknesses for generation of complex data in failing to provide for precise control of the assay and fluidics. More complex systems rely on elastomeric elements, multiple valves and complex external manipulation using up to nine actuators, and a separate rigid "exoskeleton" required for precise positioning (e.g. U.S. Pat. No. 7,718,421).

The device minimises the risk of user error, is largely mechanical, and inexpensive. It requires little training to use. The device is very well aligned with what is needed to achieve a CLIA (Clinical Laboratory Improvement Amendments) waiver and, with the sensor providing excellent control of data input and output, could even be an improvement on laboratory equipment where there are still manual elements such as barcode scanning/data recording.

Referring also to FIGS. 10 to 14, a reader 200 has an opening 220 which may be closed by a cover 221. Opening the cover 221 reveals a support mechanism for the cartridge 175, comprising a support element 210 which generally conforms to the shape of part of the cartridge 175. In the reader 200 magnetic force is applied to the cartridge 175 by reader unit magnets 203, 204, 205 and 206 on movable arms 201 and 202, respectively. The magnets (in one specific example Neodymium M12×12CON™) may be conical-shaped magnets (203, 204) for focal movement of beads or disc-shaped (205, 206), for bead mixing, according to the assay stages described above.

Heat is applied to the cartridge 175 by the thin heater element overlay 210 which covers the cartridge 175 in the space between the movable arms 201 and 202 and the exterior surface of the cartridge 175. An example is the Watlow Flexible silicone rubber heaters which have rapid heat transfer, operating temperatures to 260° C., Watt densities 12.5 W/cm2, 0.5 mm thick with an etched foil element. These are suitable for medical equipment such as blood analysers and test tube heaters. The overlay 210 heater elements are incorporated so as to be in registry with the stages of the device 175.

The reader 200 is controlled by a microprocessor linked with terminals which engage with the terminals of the sensor 168 of the device 175 when inserted. In other embodiments, point-heating may also be applied by heater elements incorporated into the movable arms 201 and 202. There also may be a heater element underneath a lysate vessel 120, adjacent the flat portion of the vessel.

The chip 168 is mounted on a protruding connector 169 with four gold fingers (VDD, GND, Sclk, SDa), for electrical mating with a connector in the reader unit. A heater and temperature sensor on the chip 168 may also facilitate heating and melting of Probe-2 in the reservoir 164, with real-time feedback and assay monitoring by the temperature sensor, for precise assay temperature control around the melting point. This is a major advantage of using a disposable chip within the cartridge. The chip 168 is immersed and sealed in the microfluidic cartridge. The chip has multiple sensors—32 sensors in this embodiment.

The 32 sensors have 32 PNA probes immobilised on their surface by spotting during chip or cartridge manufacture. R-bead hybridisation to the surface occurs as per the assay described for the multiplex assay earlier, however there are up to 32 targets rather than two. There are therefore 32 sets of PNA probes in the assay. The assay proceeds as outlined in the multiplexing assay above. After R-bead separation, the T-beads are removed to a waste area 149.

In some assay embodiments the R-beads may be non-magnetic (e.g. gold or oxide nanoparticles), which also facilitates this separation.

Mechanical Screw Drive

A column of liquid over the sensor chip in the reservoir 164 is gently moved over and back across the sensor surface by gentle oscillation and pressure of a piston 176, driven by a screw-actuator 177 which engages with the external reader unit. This causes gentle liquid mixing of the beads during the incubation period (5-30 mins), and facilitates bead tethering to 32 sensors. The number of R-beads attached to each sensor is proportional to the number of RNAs in the sample initially. After tethering, liquid is then removed from the sensor surface, by pressure of the piston 176, into an expansion chamber 179 which contains air (or dry nitrogen). A wash solution 178 is pushed ahead of the gas over the sensors. When the gas is over the sensors, a 'dry' capacitance reading is taken as before, and a lower-limit-of-quantification of less than 100 beads. Please refer again to FIG. 2(c) for an example image of this.

In one embodiment mixing can be achieved by applying a voltage across the microfluidic channel generating an electroosmotic flow, which will move the R-beads back and forth across the sensor surface. In one embodiment mixing over the sensor chip can be achieved through addition of an electrokinetic device within the microfluidic channel which generates turbulence within the liquid.

A waste region 149 is incorporated, into which the displaced liquid (and molten wax; chip reservoir buffer; surfactant; and any gas) may be pushed. This is precisely designed to contain a volume of sterile gas which is pushed in front of this liquid through a HEPA filtered vent 170 to the environment. This equilibrates the pressure within the cartridge and allows easier tolerances within the design and manufacture of the cartridge.

The only connection of the cartridge to the environment is filtered and only air is expelled through it. All biological material (even including the target RNA) is retained within, which makes this cartridge safely disposable. The lack of any fluidic connection to the reader is a major advantage of the invention.

In another embodiment, a collapsed elastomeric/membrane region within the vent provides for pressure equilibration which does not involve any connection to the environment and thereby the cartridge is completely sealed during and after use.

The device 160 of FIG. 5 has a final reservoir 164 containing an organic liquid with a much lower dielectric constant than water (e.g. ethanol). Where there are large numbers of R-beads and the R-beads are magnetic, these may be moved on to the sensor and the R-beads measured against the organic liquid rather than air (dielectric constant of 1). No drying is performed.

Similarly, in a multiplex embodiment, the cartridge 160 may have a final reservoir containing an ethanol solution. PNA-PNA binding is possible in this scenario and, as such, the multiplexing assay can be accomplished. An organic solvent can be removed by allowing evaporation or active heating.

In embodiments containing organic solvents, it will be clear that the lower density allows gravity to assist R-beads to drop across (vertical configuration) or down (horizontal configuration) on to the chip faster due to their lower buoyancy in the organic solution. This is desirable for some applications.

In another embodiment, T-beads, which are magnetic and designed to be buoyant in water, can be manipulated using external magnetic fields within solutions less dense than water (e.g. 20% ethanol). Consequently, T-beads can still be removed from the reservoir above the chip. However, an R-bead which is less buoyant in aqueous solution and which is untethered from a T-bead above the chip will have an increased tendency to sink on to the surface of the chip. This is desirable to promote rapid sinking of the R-beads on to the surface of the chip in this embodiment. A reader which supports the cartridge horizontally may be used.

Actuation System

Referring again to FIGS. 12 to 14, the actuation system mediates engagement of external magnetic fields is a sub-assembly within the reader. One embodiment involves the use of linear actuators for precise movement of an arm mechanism in the X-, Y- and Z-axes. The arm is branched in two, one on either side of the cartridge system, and set back about 2 cm from the LEFT and RIGHT sides of the cartridge system, respectively. On the arms there are mounted at least three permanent magnets, e.g. Neodymium Rare Earth Magnet Apex Magnets M12×12CON; M20Wdg; M121418 diamR. These magnets are mounted in such a way on the arms so that the net magnetic field on the cartridge is minimal when they are set to their neutral position, equidistant from the centre of the cartridge. However, when the arm is actuated in the plus or minus direction in the X axis, the magnet on one or other arm is engaged and any magnetic beads within that field are drawn towards it. As the arm can also be moved in the Y- and Z-axes, beads can be moved accurately in three dimensions within the microfluidic.

In another embodiment, the arm of at least one actuator is connected to a commercially available actuation system as is used in an electric toothbrush, such as Philips Sonicare™. This sonication frequency (200-400 Hz) and complex sweeping movement provides for effective cleaning of dental surfaces in combination with a brush head. However, surprisingly, the underlying automated mechanism found within, when activated create a weak electromagnetic field or when joined with a neodymium magnet, as above, provides for an unexpected mixing and homogenising effect on magnetic beads within a microfluidic. Improved kinetics for target capture are also possible. The costs of these actuators are low due to their mass manufacture for this common household item.

In one embodiment, a small sonication device such as a piezo actuator is applied directly to the outside of individual wash and attachment chambers which leads to an effective mixing of particles within these chambers. In one embodiment, a combination of sonication and magnetic mixing is used.

The movement of the arms 201 and 202 and thus the magnets 203 and 204, and heater elements on the magnets 205 and 206, is dynamically controlled by a programmed controller as required by the various stages of the system. This enables fully automated operation of the system by an untrained operator, once the blood sample has been taken.

Heaters incorporated into the magnets 205 and 206, and possibly also in the magnets 203 and 204 may operate as point heaters. These may heat through the magnets or around them, provided the heaters do not heat the magnets excessively (whereby they start to lose magnetism—the Curie temperature). In another embodiment, a 3D arrangement of a magnet on an XYZ drive may be used for sample agitation.

Cartridge and Reader Electronic Circuit

In one example, the cartridge processor drives operation of the reader to perform the appropriate assay.

In a preferred embodiment, the cartridge processor and memory contains all of the information for a particular cycle of cooling, heating, detailed X-Y-Z actuator movement, incubation times or other data for controlling operation of the reader for performing the assay for which the cartridge is designed. This embodiment removes multiple steps seen in other point of care cartridge systems where the user must scan barcodes and select assays. In this embodiment the need for a graphical user interface is eliminated entirely, and replaced by a very simple LED "traffic light system" indicating to the user that a test has been successfully completed.

In one embodiment, a barcode can contain a reference ID for a particular cycle of cooling, heating, detailed X-Y-Z actuator movement, incubation times or other data that the system reader could reference. This will require database access for the reader to a corresponding set of information for each of these variables. This database has comprehensive data and instructions for each potential cartridge that could be used on the reader. In another embodiment, the cartridge chip contains the reference ID.

Cartridge Authentication

The system can be compatible with platforms such as Alexa or Google Home. This allows a remote clinician to assess reported data accurately, directly from the device. This may allow the remote clinician to follow up on a test with the patient and pass on instructions on further tests to be carried out either immediately or over a period. It will also enable automated ordering of further tests required to be delivered to the user. Connection to such platforms may also allow spoken or visual commands to be issued to the reader device.

In one embodiment, the user must interact with the device using an authentication software application, "app", wherein a smartphone or tablet individual to the user is used with the cartridge and cartridge reader. In this embodiment, the cartridge cannot be used unless it receives a unique user identifier which locks that disposable cartridge to user. In one embodiment, the user must provide a PIN/fingerprint to the app running on their personal computing device and this then transmits this code to the reader (or cartridge directly in case of a wireless silicon chip) which then writes this individual code to the chip. A suitable technology for this communication could be near field communication chips on the reader and personal device. Advantageously, any data generated by the cartridge is automatically associated with the user. The unique, secure identifier is stored on the chip within the disposable cartridge. On completion of the assay, the chip will not return its data unless it is presented by the matching code on the device used by the individual user to generate the code stored on the cartridge (e.g. using NFC). The chip data is transferred to the user device and all processing of the data (e.g. generation of an output or secure transfer of the data to a storage system, including third parties) is handled by software on the user device. Additionally, the cartridge may be safely disposed of as a third party recovering the cartridge will not be able to read the cartridge without the individual user device. This embodiment can securely lever off the security features, processing power and connectivity of the personal device, thus simplifying the technology which needs to be on the reader itself, keeping the cost of that device low—it is a "slave" for the cartridge which may program its movement and a simple interpreter for the external personal device which handles data processing, transmission and interpretation for the user.

The on-chip non-volatile memory can take a time date stamp and a GPS location so that it is clear when and where the test has been carried out. I could also be possible to "lock" a cartridge so that it can only be used at a certain location or at a certain time. A valve system could be incorporated so that a sample cannot be introduced into the cartridge until it has received a time/location stamp by pre-inserting into the reader device.

Such security features may be provided on a device which has a different arrangement of assay stages, and possibly not including an inlet with a lysing agent.

Alternative Device Physical Conduit Arrangement

FIG. 15 shows an alternative assay cartridge physical arrangement of conduits and reservoirs, 300, suitable for 3D-printing construction. This has a lysis chamber 302 and stages 310, 311, 312, and 314 performing the same functions as the assay stages of the other embodiments, and terminating in a 3D-printed sensor electrode structure 313.

Blood-to-Result Device

In a conventional technique for taking a blood sample a butterfly needle is used to take the sample form a patient's hand and it is delivered via a catheter into an evacuated collection tube. The phlebotomist may have several blood-collection tubes ready, to take multiple patient samples for multiple subsequent laboratory tests. A 5 ml tube for example is 13 mm diameter and 100 mm long. Once the venepuncture is performed with butterfly needle and catheter which is affixed to the patient, evacuated tubes (e.g. 'Vacutainer' from BD Inc.) are then inserted to the catheter safety tube holder, each drawing blood via the catheter and pierced rubber seal—which re-seals itself upon withdrawal of the tube.

The lysis chamber of the described device may be of 13 mm diameter for example, configured to rapidly and simply slot into the same safety tube holder and needle. It may for example be 60 mm long, for a total sample of up to 3 ml for example. The inlet stage may have a chamber which is evacuated during manufacture and thus constructed of a robust and vacuum resistant material. The filter may be a plasma/serum separation filter, a standard blood separation membrane, e.g. Novilytic or Indira of 200 µm to 400 µm thickness, comprising several layers, each with different pore sizes, for example 50 um to 100 um pores on the whole-blood side, and 0.8 µm to 2 µm pore diameter on the plasma/serum side. These successively filter out each of the different blood cells and particles, with yields of typically 60% to 80%.

In various embodiments a device of the invention has an inlet stage with a piston for urging a raw sample such as blood through filter. The remainder of the device may be of any of the embodiments described above. This allows a workflow which is analogous to the standard phlebotomist workflow, facilitating simple rapid blood sample collection.

Referring to FIG. 16 an inlet stage 500 comprises a lysis housing 501 supporting a filter 502 at annular supports 503. There is a membrane 504 supported by annular supports 505 for injection of a blood sample into a volume 510 made up of not only the space between the membrane 504 and the filter 502 but also a space within a chamber 506 downstream of a piston 515 operated by a screw mechanism 516.

In more detail, the membrane 504 is a self-sealing membrane for blood inlet via a phlebotomist needle. The chamber 506 is a vacuum chamber providing an excess vacuum region into which whole blood is drawn. A space 520 downstream (above) the filter 502 is a lysate region containing, in use, plasma. The piston 515 provides positive pressure on the volume 510 in a manner which does not affect the integrity of the housing 501. The screw mechanism 516 may be dedicated as illustrated. However, it may alternatively be the screw mechanism 176/177 of the device 175 if the lysis chamber 500 were incorporated in such a device. Hence the screw mechanism would have a dual purpose, one for sample inlet and one for sample management over the sensor. The filter 502 is a whole blood filter of known type suitable for filtering plasma, held in place against pressure by the mechanical braces 503. The space 530 contains wax containing capture, T-beads. If the device 500 were attached to a microfluid cartridge device such as 175 it may be regarded as a 'sample to result' device, with no sample-prep requirement; upon removal from the patient catheter tube, it can be immediately placed in a reader unit for simple and rapid NA detection and quantification.

In use, a phlebotomist needle pierces the self-sealing membrane 504, allowing whole blood to enter the vessel, filling the volume 510 including both the immediately adjacent volume 510(a) and the adjoining overflow/excess region 510(b). The needle is withdrawn. Positive pressure is applied by the piston 515 to drive blood through the filter 502 until the target sample plasma volume 520 is achieved. The self-sealing membrane 504 withstands the pressure applied to the system.

Referring to FIG. 17 an inlet stage 600 has a lysis chamber 601 with a wax/bead plug 602. There is a pre-filter 603 and a blood filter 604 on the downstream side of which there is a lytic agent such as Chelex. A housing wall 610 forms an evacuated chamber 620(a) acceded by a self-sealing membrane 611 through which a needle 612 may be inserted. The volume 620(a) is linked with a volume 620(b) having a piston 621 operated by a mechanism 622. A wall 625 diverges from a path from the piston 621 to the filter 603 to form a side volume for entrapment of bubbles.

In use, the needle 612 is inserted at 90° so that the whole blood and any bubbles fill the whole volume 620. The device may be turned through 90° so that any bubbles rise into the volume 626. Positive pressure applied by the piston 621 pushes plasma through the pre-filter 603 and the blood filter 604, for contact with the lytic agent 627 and the beads 602.

FIG. 18 shows a direct in-line inlet stage 700 having a housing 701 supporting a pre-filter 704 and a blood filter 705 downstream of which there is a chamber 703 for lysis and in turn a wax/bead plug 702. A piston 706 is on the longitudinal axis of the filters 704 and 705. A self-sealing membrane 712 is mounted in the housing 701 at 90° to this axis and there is a bubble-entrapment volume 711 aligned with the membrane, so that if the membrane is horizontal the trap 711 can capture any bubbles as they rise to the surface. This reduces the presence of any air or unfilled vacuum which might be pushed by the piston 706 through the filter. This diagram shows a needle N being inserted, surrounded by a protective sleeve S as is well known. FIG. 18 also shows application of the inlet stage 700 to the device 100 of FIG. 1. As shown, the needle N is used to directly inject the blood through the self-sealing membrane 712, illustrating graphically how there is blood-to-result operation.

The application of heat and/or other lytic agents cause lysis of any targets in the plasma (e.g. HIV viral particles) and melting of the wax, releasing PNA-coated T-beads which capture the HIV DNA. The magnetic beads are pulled into the wax and processed as for the other embodiments.

FIGS. 19 and 20 show an alternative inlet stage 750, having a main body 751 on a handle portion (or "cap") 752 with hand-grip knurls 755 and a round wall 756 defining a socket for the main body 751. The handle portion 752 also has a membrane 757 resilient material for penetration by a needle for injection of the sample. The main body 751 has an air trap 766 which in use provides an air trap above a sample 771 for bubbles to gather. The other side has a passageway 765 with a wax plug 772 within which the beads are embedded. The beads flow out through an outlet 770. This inlet stage does not have a filter, and so is suitable particularly for use with whole blood samples.

Advantages

The invention does not require laboratories, refrigerators, or any complex laboratory equipment. The cartridge is completely sealed, with only an electrical connection to the reader. The sample and all reagents are retained internally, enabling very safe use and disposal. The act of lysing any viral particles which are introduced into the cartridge renders them inert, thus removing any infection risk should the device be forcibly damaged during disposal. The reader unit can operate on a rechargeable battery e.g. lithium ion, lithium polymer. This enables RNA viral-load testing to be carried out without the need for a laboratory, and in small community and rural clinics, where it is often most needed, to rapidly intercept and diagnose disease outbreaks, and enable rapid point-of-care diagnosis and prescription of correct treatment, to stop further virus and disease spreading.

The assay employs synthetic PNA probes, beads, a semiconductor chip, oil/wax barriers, and DI water. The stability of these, and the lack of enzymes, proteins, and polymerases, makes the cartridge very robust and simple to manufacture. Logistical cost savings include removing the need for blue or dry ice for transport and better shelf life (e.g. expensive stockpiles of PCR reagents for public health/biodefence tests are not required). The interfacial tension and capillary forces between the water and oil/wax barriers keeps the aqueous solution reservoirs isolated from each other. This replaces valving, greatly simplifying the design and manufacture of the cartridge This also reduces complexity in the reader, saves on manufacture costs, and reduces the risk of device failure over time. It also enables wide temperature excursions of the cartridge during different parts of the assay (e.g. 90-95° C. during a lysis step; 37-70° C. during an RNA target annealing step; 90° C. during an RNA melting step or PNA-PNA specificity step), and wide temperature excursions during shipping and distribution, without any side effects. This is particularly important in eliminating dry-ice shipping requirements—a major barrier to widescale point-of-care diagnostic deployments.

Advantageously, the device also enables self-testing and calibration of the spotted sensors during wafer-level testing. The stability of the synthetic PNA probes is advantageous for wafer level processing which would be difficult for standard DNA or protein markers. This allows wafer level functionalization of the chip sensors prior to downstream testing, calibration, and processing. As the converters and digital calibration circuits in the CMOS sensor chip are located directly beneath the sensor pads, it allows for testing and calibration of the precise amount of probe spotted on each sensor to be carried out easily as well as facilitating the recording of these calibrations in an on-chip non-volatile memory. This is important for quantification of captured targets by the clinical end-user.

This built-in self-testing and calibration capability is a major advantage over optical DNA microarrays, which can't be tested and calibrated individually, due to testing being destructive with optical probe attachment.

An advantage of having functionalization and calibration data stored in an on-chip non-volatile memory is the ability to run quality control checks on the sensor at each stage of the functionalisation and during and after cartridge assembly. The data from this QC check can then be compared to the original calibration data collected during sensor functionalization to determine whether there had been any damage caused to the sensor area during packaging or transportation or assembly. This feature helps to lessen the chance of false negative readings due to possible poor functionalisation or manufacture/transport related damage to the chip. Similarly, such data can be used on insertion of the cartridge into the reader by the end-user as part of pre-assay quality control checks.

The sensor circuit may include a CMOS IC which has a temperature sensor incorporated. One important advantage of an internal temperature sensor is that it can be used to determine the temperature of the cartridge before the use begins. Due to differing ambient temperatures in different environments the temperature of the cartridge could vary greatly. Heating the cartridge to a set temperature (e.g. 35° C.) before running the assay will help to avoid constraining cartridge storage conditions, allowing storage at variable room temperatures. Whilst the set start temperature can be achieved by using the heater in the reader unit, it can be monitored by the temperature sensor in on the sensor (for example CMOS IC chip). Feedback from the sensor chip to the reader can assure that the desired set-point, initial temperature is reached regardless of ambient affects.

A version of the reader unit can be provided for hot climates, which includes a cooling system such as a Peltier system, which can then be capable of cooling the cartridge to the desired set-point, initial temperature.

Alternatives

In various embodiments the device does not have an inlet with a lysing agent, as this can be done externally and a pre-lysed sample may be injected into the inlet. Also, the sensor may not be a capacitive sensor. Use of a capacitance sensor is particularly advantageous because it can readily quantify the target analyte by bulk measurement of capacitive response of beads representing the amount of target analyte. However, the sensor may for example operate on the basis of other electrical properties such as resistance or inductance, or indeed it may be optical on the basis of fluorescence of beads as is well known in the art.

The cartridge could also work as a "smart" blood storage container. The patient ID is recorded on the chip EEPROM memory using a direct or wireless connection. The identifier can be further linked with a 2D barcode printed on the cartridge.

While we have described a cartridge for immediate analysis, it may be necessary for suitable additives to be included for blood storage within the inlet prior to further processing. The ability to store the sample stably within the disposable system in a small format is advantageous for some end-user logistics. In this embodiment, the user conducting collection needs to link the cartridge to the patient in a database. This may be done by scanning a 2D barcode on the cartridge; and by writing the patient ID to the EEPROM memory in the sensor chip within the cartridge, which can be transferred to another user/nurse for processing. This may be logistically efficient in a primary health care setting where blood collection and processing could be both accomplished in the same facility by staff with little training. The person conducting the processing does not know whose sample it is or even what test is being conducted, as this latter information is also stored on the chip and transferred to the reader automatically. This has important advantages for patient privacy.

It is envisaged that a reservoir may be filled with an organic solvent such as ethanol. Attached to the reservoir is a Fluorosilicone (or other ethanol resistant material) plug which when removed allows the ethanol within to evaporate. PNAs can bind in the presence of ethanol.

Where the device has an agitator, it may comprise a piston for pushing and pulling analyte over the sensor, and such a piston may be driven by a screw mechanism or any arrangement of linearly-moving member such as a small solenoid. It may alternatively comprise a vibrating actuator such as a piezo actuator mounted internally or externally on the device housing. The bead movement which is imparted may be longitudinal or rotary.

The R-beads may be separated from the T-beads and NA by any one or more of a number of mechanisms such as by application of heat to melt the PNA-Probe2 links to the NA, or by chemically destroying the NA target, thus breaking the tether between the two beads, or by use of a decoupling probe which is complementary to any of the probes in the link and which frees the target by preferential binding to a probe and not the target. Where the channel is heated it may be by conduction through the device body, and the wall may be up to 3 mm in thickness.

The device may include an internal control to ensure that the assay is performing efficiently. This control could be an endogenous ribosomal RNA or housekeeping gene present within the sample, or an artificial control added to the sample. This is preferably performed in a multiplexing arrangement with different probes. Detection of an R-bead corresponding to a ribosomal RNA such as 18 s which is present in blood, and varies little across eukaryotic organism, on the sensor ensures that all steps of the assay and the detection device are working.

The invention claimed is:

1. A portable diagnostic device comprising:
   a housing,
   assay stages, each with a reservoir linked by channels,
   at least one of the assay stages including a sensor for detecting target analyte,
   an inlet for receiving a sample and including:
      a sample lysing agent,
      an outlet port to the assay stages, the outlet port having a wax or oil plug having embedded magnetic beads for attachment by a probe to target analyte.

2. The device as claimed in claim 1, wherein said outlet port of the device inlet is funnel-shaped and the wax plug is a friction fit within the outlet port.

3. The device as claimed in claim 1, wherein a peptide nucleic acid PNA probe and the magnetic beads are microencapsulated in the wax or oil plug of the inlet.

4. The device as claimed in claim 1, wherein a peptide nucleic acid PNA probe and the magnetic beads are microencapsulated in the wax or oil plug of the inlet; and wherein the PNA probe and the magnetic beads are microencapsulated with one or more selected from ethyl cellulose, polyvinyl alcohol, gelatin, and sodium alginate.

5. The device as claimed in claim 1, wherein the inlet comprises a filter in a chamber and a piston arranged to drive blood through the filter.

6. The device as claimed in claim 1, wherein the inlet comprises a filter in a first chamber and a piston arranged to drive blood through the filter, the volume downstream of the piston and upstream of the filter is under vacuum; the first chamber includes a membrane which can be pierced to take a sample, and the first chamber includes the lysing agent.

7. The device as claimed in claim 1, wherein the inlet comprises a filter in a chamber and a piston arranged to drive blood through the filter; the inlet includes a bubble entrapment chamber; the bubble entrapment chamber is aligned on an axis with the membrane, and said axis is at an angle to an axis between the piston and the filter; and the bubble entrapment chamber is substantially parallel to the outlet port, the wax or oil plug preventing movement of bubbles into said outlet port.

8. The device as claimed in claim 1, wherein the inlet includes an agent to bind to a particular protein target on a viral surface which damages cell membrane integrity.

9. The device as claimed in claim 1, wherein the inlet comprises neutral beads which play no part in molecular binding but have a greater mass and/or a greater magnetism to provide for stabilisation to help the magnetic beads break interfacial tension by their greater responsiveness to an applied magnetic field.

10. The device as claimed in claim 1, wherein the channels comprise a channel communicating with the outlet port to receive said magnetic beads, said channel containing molten wax in a contiguous column and which is connected to a plurality of reservoirs formed by said assay stages so that interfacial tension and capillary force keep said assay stage reservoirs isolated from each other.

11. The device as claimed in claim 1, wherein the inlet comprises immunomagnetic beads or beads functionalized with ligands suitable for removing certain fractions of a blood sample, or the inlet comprises a bed of resinous beads which are functionalized or are coated in reagents to help prevent clotting of a blood sample.

12. The device as claimed in claim 1, wherein the assay stages and the inlet comprise a plurality of different probes on said magnetic beads and arranged to target multiple nucleic acid targets so that beads with different targets arrive on the sensor and the sensor determines the quantities of each type of bead, to provide multiplexing.

13. The device as claimed in claim 1, wherein at least one assay stage is a wash stage configured to carry out a wash.

14. The device as claimed in claim 1, wherein a conduit is arranged laterally of at least two assay stages for passage of analyte both into and out of an assay stage.

15. The device as claimed in claim 1, further comprising a heater for heating sample in the inlet and/or analyte in at least one assay stage.

16. The device as claimed in claim 1, wherein an assay stage is a reporter bead attachment stage, wherein the magnetic beads in the inlet are transport beads and are pre-attached or are arranged to attach to a first probe, and the reporter bead attachment stage contains reporter beads which have less magnetism than the transport beads, and the reporter beads have attached a second probe complementary to target nucleic acid of the analyte, such that if the target nucleic acid is present attached to a transport bead, a transport bead-reporter bead tethered sandwich is formed within the reporter bead assay stage.

17. The device as claimed in claim 1, wherein the sensor comprises a capacitive sensor arranged to detect capacitance of contents of an associated reservoir.

18. The device as claimed in claim 1, wherein the device further comprises an agitator for agitation of analyte over the sensor; and wherein the agitator comprises a piston or a sonication device, or a vibratory device.

19. The as claimed in claim 1, wherein the device comprises a device processor configured to store instructions and data required for controlling a reader and conducting an assay, and the device processor includes instructions for reader actuator movements and temperature cycles.

20. The device as claimed in claim 1, comprising a heater and/or a cooler to set an operating temperature before operation so that a desired temperature is reached independently of ambient effects.

21. The device as claimed in claim 1, wherein the device comprises a waste chamber with a vent region, into which displaced liquid such as molten wax, chip reservoir buffer, surfactant, and any gas, may be pushed.

22. A portable diagnostic system comprising a device and a reader, wherein the device comprises: a housing, assay stages, each with a reservoir linked by channels, at least one of the assay stages including a sensor for detecting target analyte, an inlet for receiving a sample and including: a sample lysing agent an outlet port to the assay stages, the outlet port having a wax or oil plug having embedded magnetic beads for attachment by a probe to target analyte, and wherein the reader comprises:

a support for receiving the device;
magnets on a drive to convey the magnetic beads through the assay stages of the device;
a heat source;
a means for communicating with the sensor of the device, and
a controller.

23. A method carried out by a system of claim 22, the method comprising the steps of:
introducing a sample into the device inlet and lysing the sample in the inlet to provide an analyte, or introducing a previously-lysed analyte into the inlet;
conveying the analyte through the assay stages within the device wherein movement and temperature of said stages are controlled, and
detecting analyte at the sensor.

24. The method as claimed in claim 23, wherein heat is applied to the inlet in order to melt the plug, resulting in the outlet port becoming unblocked and the magnetic beads being released for dispersion in the sample to capture target analyte.

25. The method as claimed in claim 23, wherein if target analyte is present, a transport bead-reporter-bead tethered sandwich is formed in an assay stage by conveying transport beads with an attached first probe and target analyte through a reporter bead attachment stage which contains reporter beads with a second probe, and wherein the magnetic drive moves so as to magnetically move the transport beads through a wash assay stage to the reporter bead attachment stage, and wherein the magnetic drive moves so as to magnetically move the beads from a reporter bead attachment stage to a reporter bead wash assay stage.

* * * * *